(12) United States Patent
Pang et al.

(10) Patent No.: US 9,891,237 B2
(45) Date of Patent: Feb. 13, 2018

(54) FLUORESCENT SENSOR FOR METAL CATION DETECTION BASED ON 2-(2'-HYDROXYPHENYL)BENZAZOLE CONTAINING A SCHIFF BASE MOIETY

(71) Applicants: Yi Pang, Copley, OH (US); Junfeng Wang, Akron, OH (US)

(72) Inventors: Yi Pang, Copley, OH (US); Junfeng Wang, Akron, OH (US)

(73) Assignee: THE UNIVERSITY OF AKRON, Akron, OH (US)

(*) Notice: Subject to any disclaimer, the term of this patent is extended or adjusted under 35 U.S.C. 154(b) by 555 days.

(21) Appl. No.: 14/340,084

(22) Filed: Jul. 24, 2014

(65) Prior Publication Data

US 2015/0031067 A1 Jan. 29, 2015

Related U.S. Application Data

(60) Provisional application No. 61/857,716, filed on Jul. 24, 2013.

(51) Int. Cl.
| | |
|---|---|
| G01N 33/00 | (2006.01) |
| G01N 33/84 | (2006.01) |
| C07D 413/12 | (2006.01) |
| C07D 413/14 | (2006.01) |

(52) U.S. Cl.
CPC .......... *G01N 33/84* (2013.01); *C07D 413/12* (2013.01); *C07D 413/14* (2013.01)

(58) Field of Classification Search
CPC ...................................................... G01N 33/84
USPC .......................................................... 436/73
See application file for complete search history.

(56) References Cited

PUBLICATIONS

Basu et al. "A novel blue luminescent high-spin iron(III) complex with interlayer OH-CI bridging: Synthesis, structure and spectroscopic studies" Polyhedron 26 (2007) 3617-3624.*
Hillebrand et al. Chemical Physics 273 (2001) 1-10.*
Nurul H. Quazi, Andrew B. Hughes, and Leann M. Tilley "Synthesis of Novel Fluorescent Compounds" Proc. SPIE 2980, Advances in Fluorescence Sensing Technology III, 270 (May 7, 1997).*
Fabiano S. Santos, Tania M. H. Costa, Valter Stefani, Paulo F. B. Goncalves, Rodrigo R. Descalzo, Edilson V. Benvenutti, and Fabiano S. Rodembusch "Synthesis, Characterization, and Spectroscopic Investigation of Benzoxazole Conjugated Schiff Bases" J. Phys. Chem. A 2011, 115, 13390-13398.*

* cited by examiner

*Primary Examiner* — Lyle Alexander
*Assistant Examiner* — Emily R. Berkeley
(74) *Attorney, Agent, or Firm* — Renner, Kenner, Greive, Bobak, Taylor & Weber

(57) ABSTRACT

Hydroxyphenylbenzazole compounds that are useful for the selective detection of zinc, aluminum, chromium, and iron cations in vitro and in vivo. The Hydroxyphenylbenzazole compounds include a 2-hydroxyphenyl group bound to a single benzazole group; a first ligand group that is a Schiff base moiety; and a second ligand group selected from a Schiff base moiety and a hydroxyl group.

17 Claims, 15 Drawing Sheets
(13 of 15 Drawing Sheet(s) Filed in Color)

FLUORESCENT SENSOR FOR METAL CATION DETECTION BASED ON 2-(2'-HYDROXYPHENYL)BENZAZOLE CONTAINING A SCHIFF BASE MOIETY

CROSS-REFERENCE TO RELATED APPLICATIONS

This application claims priority from U.S. Provisional Patent Application No. 61/857,716 filed on Jul. 24, 2013, the contents of which are incorporated herein by reference.

STATEMENT REGARDING FEDERALLY SPONSORED RESEARCH OR DEVELOPMENT

This invention was made with government support under grant No. 1R15Eb014546-01A1 awarded by the NIH. The government has certain rights in the invention.

FIELD OF THE INVENTION

The present invention generally relates to compounds that are useful to form complexes with certain metal ions, and methods for synthesizing the complexing compounds. The complexes have distinctive fluorescence responses, and thus the invention also provides in vitro and in vivo methods for the detection of metal ions.

BACKGROUND OF THE INVENTION

Significant interests exist to detect and quantify specific metal ions in live tissues or animals, as metal ions play important roles in many cellular processes and functions including gene expression and signal transduction.

Trivalent cations have important biological properties and are directly involved in the cell function where there is a critical control of $M^{3+}$ levels. For example, $Cr^{3+}$ has direct impacts on the metabolism of carbohydrates, fats, proteins and nucleic acids by either activating certain enzymes or stabilizing proteins and nucleic acids. Chromium deficiency can increase the risk factors associated with diabetes and cardiovascular diseases. $Al^{3+}$ could also have adverse effect on human's health, as excessive amount of $Al^{3+}$ in the brain, is believed to cause neurodementia such as Parkinson's disease, Alzheimer's disease and dialysis encephalopathy. $Fe^{3+}$ plays an indispensable role in many biochemical processes at the cellular level, and in the oxygen transport processes in all tissues in the form of hemoglobin. The deficiencies or excesses of $Fe^{3+}$ can lead to a variety of diseases, such as Alzheimer's, Huntington's, and Parkinson's diseases. Thus, there is an urgent need to develop chemical sensors that are capable of detecting the presence of $Cr^{3+}$, $Al^{3+}$ and $Fe^{3+}$ ions in biological samples.

Due to their paramagnetic nature, trivalent chromium ($Cr^{3+}$) and iron ($Fe^{3+}$) are among the most effective fluorescent quenchers, which makes it difficult to develop a fluorescence turn-on sensor. For this reason, very few sensors for Cr(III) and Fe(III) have been reported, and far fewer find application in cell imaging. In contrast $Al^{3+}$ is diamagnetic, whose binding to sensors often enhance the fluorescence. Due to strong hydration of $Al^{3+}$ in water, however, most reported dyes for $Al^{3+}$ are required to be used in organic solvents or mixed solvents, with very few being suitable for $Al^{3+}$ imaging applications. Recently, the study by Costero et al. reported a fluorescein derivative, whose fluorescence at 475 nm could be turned-on by $Cr^{3+}$, $Fe^{3+}$ and $Al^{3+}$ in dry $CH_3CN$ (A. Barba-Bon, A. M. Costero, S. Gil, M. Parra, J. Soto, R. Martínez-Máñez and F. Sancenón. Chem. Commun., 2012). The presence of 4% of water in $CH_3CN$, however, will quench the fluorescence of fluorescein complex with $Cr^{3+}$ and $Fe^{3+}$ ions. It remains a challenge to design a fluorescent sensor that not only can recognize but also differentiate the trivalent cations ($Al^{3+}$, $Cr^{3+}$ and $Fe^{3+}$), especially in aqueous solution.

As the second most abundant transition-metal ion in the human body, the $Zn^{2+}$ ion is a component of enzymes and proteins, and plays an important role in various biological processes. In order to discover the vital roles of $Zn^{2+}$ in biological processes, there is growing demand for sensing $Zn^{2+}$ in living systems. Although many fluorescent chemosensors for $Zn^{2+}$ cation have been studied, few near-infrared (NIR) fluorescent zinc probes are available to give emission in the desired 700-900 nm range. An ideal $Zn^{2+}$ probe requires not only NIR emission (to minimize autofluorescence) but also large Stokes shift (for improved signal detection). It is thus desirable to incorporate the ESIPT process into the sensing scheme. Achieving the ESIPT emission signals in the NIR region, however, remains an attractive and challenging task.

SUMMARY OF THE INVENTION

A first embodiment provides a hydroxyphenylbenzazole compound containing a Schiff base moiety, the compound comprising: a 2-hydroxyphenyl group bound to a single benzazole group; a first ligand group that is a Schiff base moiety; and a second ligand group selected from a Schiff base moiety and a hydroxyl group.

A second embodiment provides a a hydroxyphenylbenzazole compound containing a Schiff base moiety as in the first embodiment, where the benzazole group is a benzoxazole group.

A third embodiment provides a hydroxyphenylbenzazole compound containing a Schiff base moiety as in the either the first or second embodiment, where the benzazole group is a benzothiazole group.

A forth embodiment provides a hydroxyphenylbenzazole compound containing a Schiff base moiety as in any of the first through third embodiments, where the benzazole group is a benzimidazole group.

A fifth embodiment provides a hydroxyphenylbenzazole compound containing a Schiff base moiety as in any of the first through forth embodiments, where the hydroxyphenylbenzazole derivative containing a Schiff base moiety includes a Schiff base defined by the formula

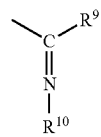

where $R^9$ is a hydrogen atom or a monovalent organic group, and $R^{10}$ is a monovalent organic group that includes an atom with a lone pair of electrons.

A sixth embodiment provides a hydroxyphenylbenzazole compound containing a Schiff base moiety as in any of the first through fifth embodiments, where the hydroxyphenylbenzazole derivative containing a Schiff base moiety includes a Schiff base selected from the group consisting of:

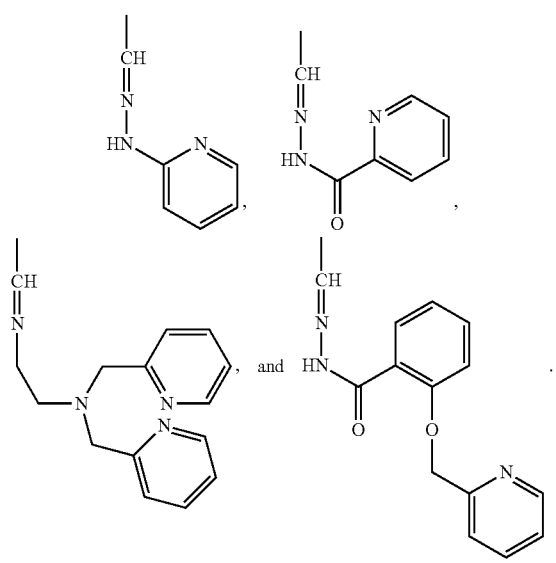

A seventh embodiment provides a hydroxyphenylbenzazole compound containing a Schiff base moiety as in any of the first through sixth embodiments, where the hydroxyphenylbenzazole derivative containing a Schiff base moiety is defined by the formula

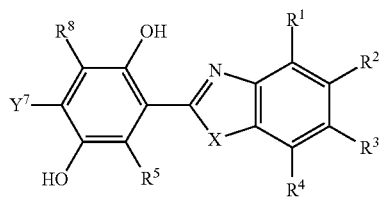

where X is an oxygen atom, a sulfur atom, a nitrogen atom with a pendant hydrogen atom, or a nitrogen atom with a pendant alkyl group; $Y^7$ is a Schiff base moiety, and $R^1$, $R^2$, $R^3$, $R^4$, $R^5$, and $R^8$ are each individually a hydrogen atom or a monovalent organic group.

An eighth embodiment provides a hydroxyphenylbenzazole compound containing a Schiff base moiety as in any of the first through seventh embodiments, where the hydroxyphenylbenzazole derivative containing a Schiff base moiety is defined by the formula

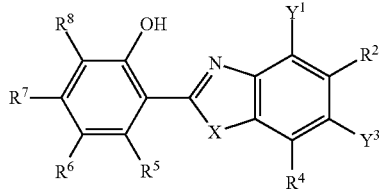

where X is an oxygen atom, a sulfur atom, a nitrogen atom with a pendant hydrogen atom, or a nitrogen atom with a pendant alkyl group; $Y^1$ and $Y^3$ are each individually a Schiff base moiety, and $R^2$, $R^4$, $R^5$, $R^6$, $R^7$, and $R^8$ are each individually a hydrogen atom or a monovalent organic group.

A ninth embodiment provides a hydroxyphenylbenzazole compound containing a Schiff base moiety as in any of the first through eighth embodiments, where the hydroxyphenylbenzazole derivative containing a Schiff base moiety is defined by the formula

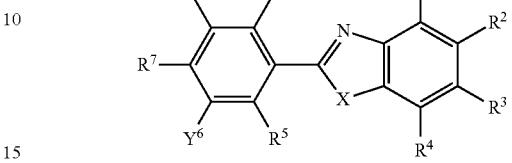

where X is an oxygen atom, a sulfur atom, a nitrogen atom with a pendant hydrogen atom, or a nitrogen atom with a pendant alkyl group; $Y^6$ and $Y^8$ are each individually a Schiff base moiety, and $R^1$, $R^2$, $R^3$, $R^4$, $R^5$, and $R^7$ are each individually a hydrogen atom or a monovalent organic group.

A tenth embodiment provides a method for detecting the presence of metal ions, comprising the steps of: (a) contacting a test sample with hydroxyphenylbenzazole compound containing a Schiff base moiety the compound comprising: a 2-hydroxyphenyl group bound to a benzazole group; a first ligand group that is a Schiff base moiety; and a second ligand group selected from a Schiff base moiety and a hydroxyl group; (b) exciting the hydroxyphenylbenzazole compound containing a Schiff base moiety with an excitation wavelength to induce a fluorescence response; and (c) observing a fluorescence response emission.

An eleventh embodiment provides a method as in the tenth embodiment, where the hydroxyphenylbenzazole derivative containing a Schiff base moiety is defined by the formula

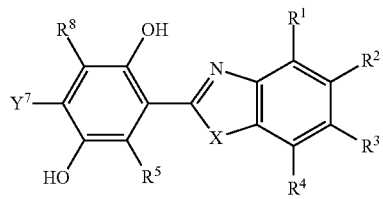

where X is an oxygen atom, a sulfur atom, a nitrogen atom with a pendant hydrogen atom, or a nitrogen atom with a pendant alkyl group; $Y^7$ is a Schiff base moiety, and $R^1$, $R^2$, $R^3$, $R^4$, $R^5$, and $R^8$ are each individually a hydrogen atom or a monovalent organic group.

A twelfth embodiment provides a method as in either the tenth or eleventh embodiments, where the hydroxyphenylbenzazole derivative containing a Schiff base moiety is used to detect a zinc ion, and the observation of a near-infrared response indicates the detection of zinc.

A thirteenth embodiment provides a method as in any of the tenth through twelfth embodiments, where the hydroxyphenylbenzazole derivative containing a Schiff base moiety is defined by the formula

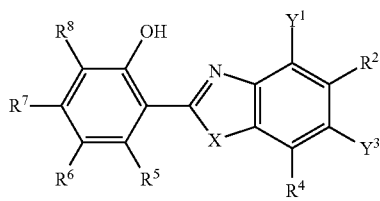

where X is an oxygen atom, a sulfur atom, a nitrogen atom with a pendant hydrogen atom, or a nitrogen atom with a pendant alkyl group; $Y^1$ and $Y^3$ are each individually a Schiff base moiety, and $R^2$, $R^4$, $R^5$, $R^6$, $R^7$, and $R^8$ are each individually a hydrogen atom or a monovalent organic group.

A fourteenth embodiment provides a method as in any of the tenth through thirteenth embodiments, where the hydroxyphenylbenzazole derivative containing a Schiff base moiety is used to detect the presence of a metal cation selected from $Fe^{3+}$, $Cr^{3+}$, and $Al^{3+}$.

A fifteenth embodiment provides a method as in any of the tenth through fourteenth embodiments, where the hydroxyphenylbenzazole derivative containing a Schiff base moiety is defined by the formula

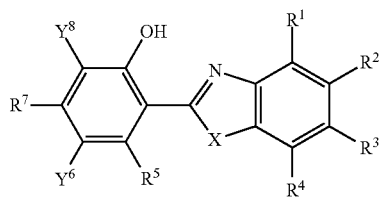

where X is an oxygen atom, a sulfur atom, a nitrogen atom with a pendant hydrogen atom, or a nitrogen atom with a pendant alkyl group; $Y^6$ and $Y^8$ are each individually a Schiff base moiety, and $R^1$, $R^2$, $R^3$, $R^4$, $R^5$, and $R^7$ are each individually a hydrogen atom or a monovalent organic group.

A sixteenth embodiment provides a method as in any of the tenth through fifteenth embodiments, where the hydroxyphenylbenzazole derivative containing a Schiff base moiety is used to detect the presence of a metal cation selected from $Fe^{3+}$, $Cr^{3+}$, and $Al^{3+}$.

A seventeenth embodiment provides a method as in any of the tenth through sixteenth embodiments, where the test sample includes living cells or a living organism.

A eighteenth embodiment provides a hydroxyphenylbenzazole compound containing a Schiff base defined by the formula

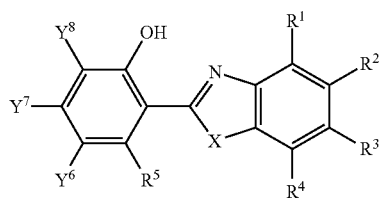

where X is an oxygen atom, a sulfur atom, a nitrogen atom with a pendant hydrogen atom, or a nitrogen atom with a pendant alkyl group; $Y^6$, $R^7$, and $Y^8$ are each individually a hydrogen atom, a Schiff base moiety, or a hydroxyl group with the proviso that at least one of $Y^6$, $R^7$, and $Y^8$ is a Schiff base moiety, and $R^1$, $R^2$, $R^3$, $R^4$, and $R^5$ are each individually a hydrogen atom or a monovalent organic group.

A nineteenth embodiment provides a method of preparing a hydroxyphenylbenzazole compound containing a Schiff base comprising: reacting an aldehydephenylbenzazol compound with a compound that includes and amino or hydrazine moiety; where the aldehydephenylbenzazol compound is defined by the formula

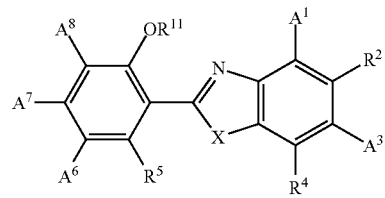

where X is an oxygen atom, a sulfur atom, a nitrogen atom with a pendant hydrogen atom, or a nitrogen atom with a pendant alkyl group; $A^1$, $A^3$, $A^6$, $A^7$, and $A^8$ are each individually a hydrogen atom, an aldehyde group, or an ester group, with the proviso that at least one of $A^1$, $A^3$, $A^6$, $A^7$, and $A^8$ is a aldehyde group; $R^{11}$ is a monovalent organic group; and $R^2$, $R^4$, and $R^5$ are each individually a hydrogen atom or a monovalent organic group.

A twentieth embodiment provides a method as in the nineteenth embodiment, where the compound that includes and amino or hydrazine moiety is selected from

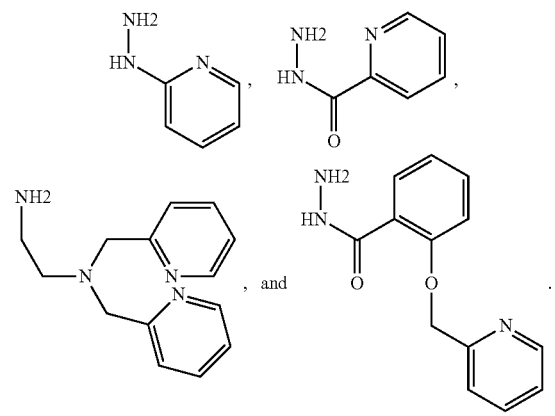

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF ILLUSTRATIVE EMBODIMENTS

Figure 1:
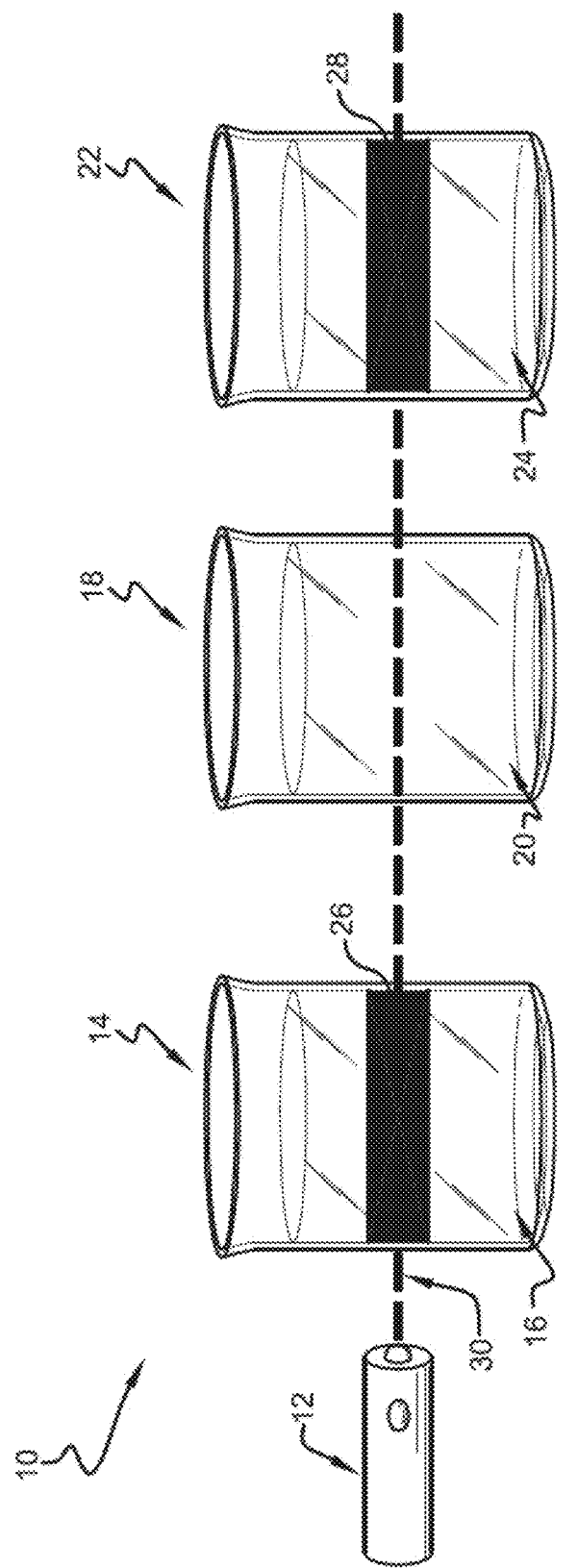
FIG. 1 provides a general schematic of a method for testing one or more test solutions for the presence of metal ions in accordance with this invention.

Embodiments are based, at least in part, on the discovery of a process for detecting metal ions, which uses a hydroxyphenylbenzazole compound containing a Schiff base moiety. Advantageously, it has been found that by varying the location of the Schiff base moiety, and optionally adding a second Schiff base moiety or hydroxyl group, a hydroxyphenylbenzazole compound containing a Schiff base moiety may be tailored to detect specific metal atoms.

In one or more embodiments, the hydroxyphenylbenzazole compound containing a Schiff base moiety comprises a 2-hydroxyphenyl group bound to a benzazole group; a first ligand group that is a Schiff base moiety; and a second ligand group selected from a Schiff base moiety and a hydroxyl group.

In one or more embodiment, the hydroxyphenylbenzazole compound containing a Schiff base moiety includes a base hydroxyphenylbenzazole group. A base hydroxyphenylbenzazole group may be formed from a phenol group bound to a benzazole group. Those skilled in the art will appreciate that a benzazole groups may be defined by the formula

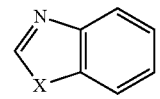

where X is an oxygen atom, a sulfur atom, a nitrogen atom with a pendant hydrogen atom, or a nitrogen atom with a pendant alkyl group. In one or more embodiments, where the X of the benzazole group is an oxygen atom, the benzazole group may be referred to as a benzoxazole group. In one or more embodiments, where the X of the benzazole group is a sulfur atom, the benzazole group may be referred to as a benzothiazole group. In one or more embodiments, where the X of the benzazole group is a nitrogen atom with a pendant hydrogen atom or a nitrogen atom with a pendant alkyl group, the benzazole group may be referred to as a benzimidazole group.

The base hydroxyphenylbenzazole group may be defined by the formula

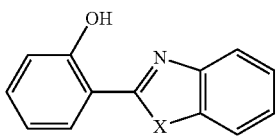

where X is an oxygen atom, a sulfur atom, a nitrogen atom with a pendant hydrogen atom, or a nitrogen atom with a pendant alkyl group. A unique feature of hydroxyphenylbenzazole compounds containing a Schiff base moiety is that the molecule contains a Schiff base moiety and optionally a hydroxyl group that are capable of complexing metals while retaining the hydroxyphenylbenzazole group. When a metal is bound to the hydroxyphenylbenzazole compound containing a Schiff base moiety, the hydroxyphenylbenzazole group allows for turn-on excited state intramolecular proton transfer (ESIPT) fluorescence.

Those skilled in the art will appreciate that a Schiff base may be defined by the formula

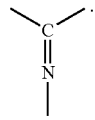

In one or more embodiments, the Schiff base moiety may be defined by the formula

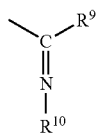

where $R^9$ is a hydrogen atom or a monovalent organic group and $R^{10}$ is a monovalent organic group. In one or more embodiments, the monovalent organic group $R^{10}$ includes an atom with a lone pair of electrons. The atom with a lone pair of electrons provides an additional location for the metal chelation. In these or other embodiments, $R^9$ may be a hydrogen atom.

Specific examples of Schiff base moieties include, but are not limited to,

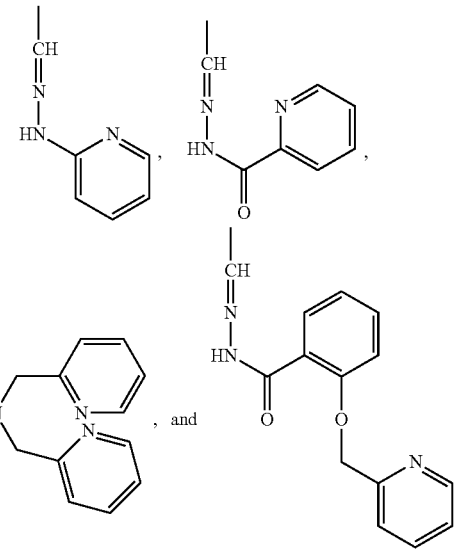

, and

In one or more embodiments, a hydroxyphenylbenzazole compound containing a Schiff base may be defined by the formula I:

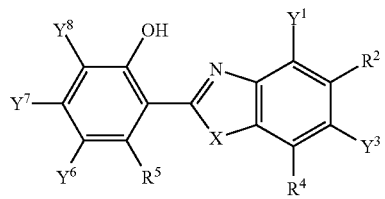

where X is an oxygen atom, a sulfur atom, a nitrogen atom with a pendant hydrogen atom, or a nitrogen atom with a pendant alkyl group; $Y^1$, $Y^3$, $Y^6$, $R^7$, and $Y^8$ are each individually a hydrogen atom, a Schiff base moiety, or a hydroxyl group, with the proviso that at least one of $Y^1$, $Y^3$, $Y^6$, $R^7$, and $Y^8$ is a Schiff base moiety: and $R^2$, $R^4$, and $R^5$ are each individually a hydrogen atom or a monovalent organic group.

In one or more embodiments, where $Y^1$ and $Y^3$ of formula I are each individually a hydrogen atom or a monovalent organic group, the hydroxyphenylbenzazole compound containing a Schiff base may be defined by the formula II:

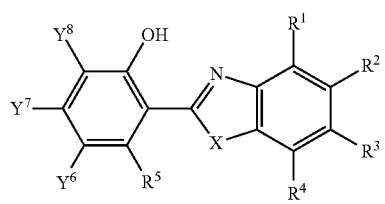

where X is an oxygen atom, a sulfur atom, a nitrogen atom with a pendant hydrogen atom, or a nitrogen atom with a pendant alkyl group; $Y^6$, $Y^7$, and $Y^8$ are each individually a hydrogen atom, a Schiff base moiety, or a hydroxyl group, with the proviso that at least one of $Y^6$, $Y^7$, and $Y^8$ is a Schiff base moiety; and $R^1$, $R^2$, $R^3$, $R^4$, and $R^5$ are each individually a hydrogen atom or a monovalent organic group.

In one or more embodiments, where $Y^1$, $Y^3$, and $Y^8$ of formula I are each individually a hydrogen atom or a monovalent organic group, and $Y^6$ is a hydroxyl group, the hydroxyphenylbenzazole compound containing a Schiff base may be defined by the formula III:

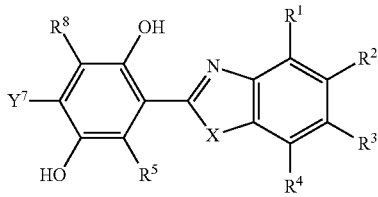

where X is an oxygen atom, a sulfur atom, a nitrogen atom with a pendant hydrogen atom, or a nitrogen atom with a pendant alkyl group; $Y^7$ is a Schiff base moiety, and $R^1$, $R^2$, $R^3$, $R^4$, $R^5$, and $R^8$ are each individually a hydrogen atom or a monovalent organic group.

In one or more embodiments where $Y^6$, $Y^7$ and $Y^8$ of formula I are each individually a hydrogen atom or a monovalent organic group, the hydroxyphenylbenzazole compound containing a Schiff base may be defined by the formula IV:

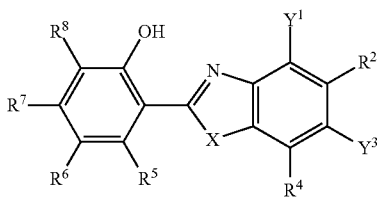

where X is an oxygen atom, a sulfur atom, a nitrogen atom with a pendant hydrogen atom, or a nitrogen atom with a pendant alkyl group; $Y^1$ and $Y^3$ are each individually a Schiff base moiety, and $R^2$, $R^4$, $R^5$, $R^6$, $R^7$, and $R^8$ are each individually a hydrogen atom or a monovalent organic group.

In one or more embodiments where $Y^1$, $Y^3$, and $Y^7$ of formula I are each individually a hydrogen atom or a monovalent organic group, the hydroxyphenylbenzazole compound containing a Schiff base may be defined by the formula V:

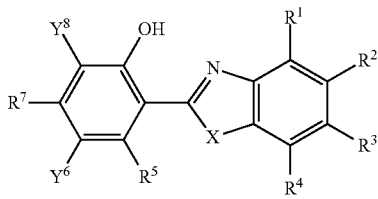

where X is an oxygen atom, a sulfur atom, a nitrogen atom with a pendant hydrogen atom, or a nitrogen atom with a pendant alkyl group; $Y^6$ and $Y^8$ are each individually a Schiff base moiety, and $R^1$, $R^2$, $R^3$, $R^4$, $R^5$, and $R^7$ are each individually a hydrogen atom or a monovalent organic group.

In one or more embodiment, the hydroxyphenylbenzazole compound containing a Schiff base may be prepared by reacting an aldehydephenylbenzazol compound with a compound that includes and amino or hydrazine moiety; where the aldehydephenylbenzazol compound is defined by the formula

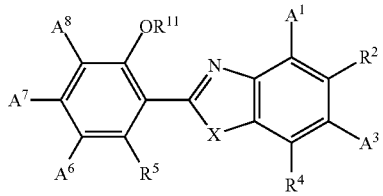

where X is an oxygen atom, a sulfur atom, a nitrogen atom with a pendant hydrogen atom, or a nitrogen atom with a pendant alkyl group; $A^1$, $A^3$, $A^6$, $A^7$, and $A^8$ are each individually a hydrogen atom, an aldehyde group, or an ester group, with the proviso that at least one of $A^1$, $A^3$, $A^6$, $A^7$, and $A^8$ is a aldehyde group; $R^{11}$ is a monovalent organic group; and $R^2$, $R^4$, and $R^5$ are each individually a hydrogen atom or a monovalent organic group.

Suitable compounds compound that includes and amino or hydrazine moiety include, but are not limited to,

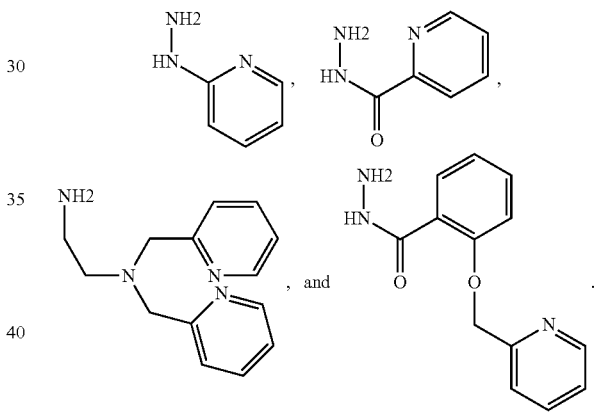

Suitable monovalent organic groups may be electron donating or electron withdrawing groups. Examples of electron donating groups, also referred to as activating groups, are groups that add electron density to the benzene ring. Electron donating groups are typically classified by their strength into groups consisting of strong electron donating groups, moderate electron donating groups, and weak electron donating groups.

Examples of strong electron donating groups include, but are not limited to, an alcohol group (—OH), an oxyl group (—O⁻), an amino group (—NH$_2$), alkylamino groups (—NHR), and dialkylamino groups (—NR$_2$). Examples of moderate electron donating groups include, but are not limited to, alkoxy groups (—OR) and amide groups (—NH-COR). Examples of weak electron donating groups include, but are not limited to, alkyl groups (—R). For the purpose of defining donating groups, each R may be independently defined as an alkyl group. In one or more embodiments alkyl groups include linear or branched hydrocarbons with a carbon chain length of 1 to 6 carbons. Specific examples of alkyl groups include, but are not limited to, methyl, ethyl, propyl, isopropyl, isobutyl, tert-butyl, n-butyl, sec-butyl, isopentyl, tertpentyl, n-pentyl, sec-pentyl, terthexyl, n-hexyl, isohexyl, and sec-hexyl.

Specific examples of alkylamino groups suitable for use as an electron donating group include, but are not limited to, methylamino, ethylamino, propylamino, isopropylamino, isobutylamino, tert-butylamino, n-butylamino, sec-butylamino, isopentylamino, tertpentylamino, n-pentylamino, sec-pentylamino, terthexylamino, n-hexylamino, isohexylamino, and sec-hexylamino.

Specific examples of dialkylamino groups suitable for use as an electron donating group include, but are not limited to, dimethylamino, diethylamino, dipropylamino, diisopropylamino, diisobutylamino, di-tert-butylamino, di-n-butylamino, di-sec-butylamino, diisopentylamino, tertpentylamino, di-n-pentylamino, di-sec-pentylamino, di-tert-hexylamino, n-hexylamino, diisohexylamino, di-sec-hexylamino, methylethylamino, methylpropylamino, methylisopropylamino, methylisobutylamino, tert-butylmethylamino, n-butylmethylamino, ethylpropylamino, ethylisopropylamino, ethylisobutylamino, tert-butylethylamino, and n-butylethylamino.

Specific examples of alkoxy groups suitable for use as an electron donating group include, but are not limited to, methoxy, ethoxy, propoxy, isopropoxy, isobutoxy, tert-butoxy, n-butoxy, sec-butoxy, isopentoxy, tert-pentoxy, n-pentoxy, sec-pentoxy, tert-hexoxy, n-hexoxy, isohexoxy, and sec-hexoxy.

Specific examples of amide groups suitable for use as an electron donating group include, but are not limited to, acetamide, propanamide, butyramide, isobutyramide, pentanamide, isopentanamide, and tertpentanamide.

Electron withdrawing groups, also referred to as deactivating groups, are groups that remove electron density from the benzene ring. Electron withdrawing groups are typically classified by their strength into groups consisting of strong electron withdrawing groups, moderate electron withdrawing groups, and weak electron withdrawing groups.

Examples of strong electron withdrawing groups include, but are not limited to, a nitro group (—$NO_2$), quaternary amine groups (—$NR_3$), and trihalomethane groups (—$CX_3$). Examples of moderate electron withdrawing groups include, but are not limited to, a cyano group (—C≡N), a sulfonate group (—$SO_3H$), a carboxylic acid group (—COOH), ester groups (—COOR), an aldehyde group (—CHO), and ketone groups (—COR). For the purpose of defining electron withdrawing groups, R can be defined as an alkyl group described above.

Specific examples of ester groups suitable for use as an electron withdrawing group include, but are not limited to, methanoate, ethanoate, propanoate, butanoate, pentanoate, and hexanoate.

Specific examples of ketone groups suitable for use as an electron withdrawing group include, but are not limited to, ethanoyl, propanoyl, butanoyl, pentanoyl, and hexanoyl.

In one or more embodiments, the R groups of formulas I, II, III, IV, and/or V, may be individually selected from alkyl groups and hydrogen atoms. In these or other embodiments, the R groups of formulas I, II, III, IV, and/or V, may be hydrogen atoms.

In one or more embodiments, a method for detecting the presence of metal ions is provided, comprising the steps of: (a) contacting a test sample with a hydroxyphenylbenzazole compound containing a Schiff base moiety the compound comprising: a 2-hydroxyphenyl group bound to a benzazole group; a first ligand group that is a Schiff base moiety; and a second ligand group selected from a Schiff base moiety and a hydroxyl group; (b) exciting the hydroxyphenylbenzazole compound containing a Schiff base moiety with an excitation wavelength to induce a fluorescence response; and (c) observing a fluorescence response emission.

Contacting a test sample with hydroxyphenylbenzazole compound containing a Schiff base moiety includes adding a hydroxyphenylbenzazole compound containing a Schiff base moiety to a test sample in any matter of addition. The hydroxyphenylbenzazole compound containing a Schiff base moiety may be added to a test sample neat or in solution. In embodiments, where the test sample is an organism or cells from an organism the hydroxyphenylbenzazole compound containing a Schiff base moiety may contact the test sample through ingestion and injection.

As noted above, hydroxyphenylbenzazole compounds containing a Schiff base moiety may be tailored to complex specific metal atoms. In one or more embodiments, hydroxyphenylbenzazole compound containing a Schiff base moiety for the detection of zinc compounds include a Schiff base moiety and a hydroxyl group situated on the base hydroxyphenylbenzazole group so that they may complex zinc. Hydroxyphenylbenzazole compounds containing a Schiff base moiety that may be used to detect zinc may be referred to as zinc-complexing hydroxyphenylbenzazole compounds.

In one or more embodiments, a hydroxyphenylbenzazole compound containing a Schiff base moiety may be used to detect zinc. Suitable hydroxyphenylbenzazole compounds containing a Schiff base moiety for the detection of zinc include those defined by the formula III:

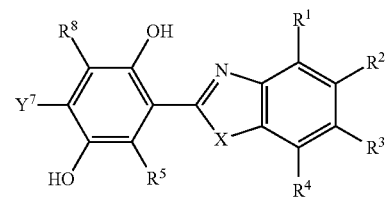

where X is an oxygen atom, a sulfur atom, a nitrogen atom with a pendant hydrogen atom, or a nitrogen atom with a pendant alkyl group; $Y^7$ is a Schiff base moiety, and $R^1$, $R^2$, $R^3$, $R^4$, $R^5$, and $R^8$ are each individually a hydrogen atom or a monovalent organic group.

Examples of hydroxyphenylbenzazole compounds containing a Schiff base moiety for the detection of zinc include, but are not limited to,

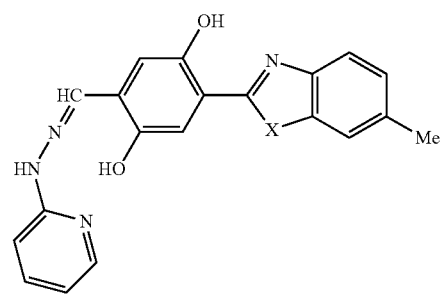

where X is an oxygen atom, a sulfur atom, a nitrogen atom with a pendant hydrogen atom, or a nitrogen atom with a pendant alkyl group.

Zinc-complexing hydroxyphenylbenzazole compounds, when irradiated with an excitation wavelength, will emit fluorescence responses at one or more wavelength(s). In one or more embodiments, the uncomplexed hydroxyphenylbenzazole compound has a single fluorescence response maxima in the visible region (e.g. $\lambda_{em}$=580 nm). In these or other embodiments, the zinc complex has two fluorescence response maxima with one in the visible region (e.g. $\lambda_{em}$=540 nm) and the other in the near infrared region (e.g. $\lambda_{em}$=720 nm).

In one or more embodiments, the zinc-complexing hydroxyphenylbenzazole compound may be used to detect the presence of zinc cations in a test sample. The test sample is a substance that may contain zinc ions. The zinc-complexing hydroxyphenylbenzazole compound is contacted with the test sample. An excitation wavelength is then applied to the test sample. In the presence of zinc cations, a zinc-complexing hydroxyphenylbenzazole compound will form a complex with a zinc ion, and the complex will give an identifiable emission wavelength or fluorescence response, thus indicating the presence of zinc cations in the test sample. In the absence of zinc cations, no zinc complex will form, and the emission wavelength will correspond to the uncomplexed hydroxyphenylbenzazole compound.

The test sample may be obtained directly from a source to be tested for the presence of zinc cations, or it may be created by dissolving or diluting a source in a solvent.

In one or more embodiments, solvents suitable for the creation of test samples include solvents selected from the group consisting of aqueous solvents, protic solvents, organic solvents, and mixtures thereof. Examples of aqueous solvents include, but are not limited to, water and pH buffered solutions. Examples of protic solvents include, but are not limited to, lower alcohols, such as methanol and ethanol. Examples of organic solvents include, but are not limited to, tetrahydrofuran and methylene chloride.

As a unique feature, the excited zinc-complexing hydroxyphenylbenzazole compound gives two emission signals upon binding to zinc cations; one emission in the visible region, and the other emission signal in the near infrared region. One advantage of this method is that it can be used to test a large number of test samples all at the same time. This is shown in FIG. 1, showing a method 10, wherein a light source 12 directs light 30 (a stimulated emission of photons) through a first container 14 holding a test sample 16, a second container 18 holding a test sample 20 and a third container 22 holding a test sample 24. As seen, the first container 14 and third container 28 hold test samples 16 that include zinc, because the light 30 causes fluorescence whose color can be seen visually as at 26 (container 14) and 28 (container 22). The second container 18 does not show fluorescence and thus, the test sample 20 placed therein does not include zinc. Although the response of the colored fluorescence signal can be detected visually by the naked eye, the signals in the near infrared region can give more sensitive detection.

The test sample may comprise or include living or dead cells from an organism, or an entire living organism or a portion of an organism that includes living or dead cells. In one or more embodiments, the zinc-complexing hydroxyphenylbenzazole compound may be used to detect the presence of zinc cations in vivo, by testing an entire living organism or a portion of an organism that contains living cells.

The zinc-complexing hydroxyphenylbenzazole compound may be added in vivo, by contacting living cells with a zinc-complexing hydroxyphenylbenzazole compound. In one or more embodiments, the living cells that are contacted by the zinc-complexing hydroxyphenylbenzazole compound are tissues or part of a living organism. Examples of methods of contacting living cells with a zinc-complexing hydroxyphenylbenzazole compound include, but are not limited to, incubating cultured cells with the zinc-complexing hydroxyphenylbenzazole compound in a culture medium, and injecting zinc-complexing hydroxyphenylbenzazole compound into living cells. Examples of methods of contacting a living organism with a zinc-complexing hydroxyphenylbenzazole compound include, but are not limited to, treating a portion of water containing an aquatic animal with a zinc-complexing hydroxyphenylbenzazole compound. Other methods of contacting a living organism with a zinc-complexing hydroxyphenylbenzazole compound include, but are not limited to, ingestion and injection.

In one or more embodiments, the presence of zinc cations in vivo may be found by exciting the living cells or living organism with an excitation wavelength. If zinc ions are present in vivo, the zinc-complexing hydroxyphenylbenzazole compound will form a complex with a zinc ion and the complex will emit an identifiable emission wavelength or fluorescence response, thus indicating the presence of zinc cations in the test sample. In the absence of zinc cations, the no zinc complex will form, and the emission wavelength will correspond to the uncomplexed hydroxyphenylbenzazole compound.

In one or more embodiments, the zinc-complexing hydroxyphenylbenzazole compound may be used to detect the presence of free zinc cations in vivo. Free zinc cations refer to the unbound zinc cations in a cell. Zinc in a cell may be bound to proteins. Zinc imbalance in certain tissues is found to be associated with several chronic diseases such as diabetes and Alzheimer's disease. Examples of tissues where free zinc cations may be found include, but are not limited to, brain, insulin, intestine, and retina.

In particular embodiments, when the zinc-complexing hydroxyphenylbenzazole compound is used to detect the presence of zinc cations or free zinc cations in vivo, it is beneficial to detect the response emission in the near infrared wavelengths. Detection in the near infrared wavelengths is advantageous because wavelengths in the near infrared region can penetrate deeper into biological tissues. In some embodiments, wavelengths in the infrared region can penetrate up to about 4 cm of biological tissue. In some embodiments, wavelengths in the infrared region can penetrate up to about 3 cm of biological tissue. In one or more embodiments, the zinc-complexing hydroxyphenylbenzazole compound may be used to detect zinc cations in an organism by measuring the emitted near infrared light.

The ability of wavelengths in the infrared region to penetrate biological tissue allows for zinc-complexing hydroxyphenylbenzazole compound to be used to scan an organism for zinc or free zinc cations. In one or more embodiments, an entire organism can be scanned for the presence of zinc cations by delivering a zinc-complexing hydroxyphenylbenzazole compound internally to an organism, exciting the entire organism with an excitation wavelength of light, and detecting the fluorescence response emission. In one or more embodiments, a portion of an organism can be scanned for the presence of zinc cations by delivering a zinc-complexing hydroxyphenylbenzazole compound internally to an organism, exciting a portion of the organism with an excitation wavelength, and detecting the fluorescence response emission. A scan of an organism, or a portion of an organism, for zinc cations can be used to create a map of zinc content within the organism. Such a map may be of benefit in the research and treating of diseases associated with the imbalance of zinc with in the organism's tissues, such as cancer, diabetes and Alzheimer's disease.

The amount of zinc-complexing hydroxyphenylbenzazole compound used to detect zinc ions can be defined in terms of nanomoles (nM). In one or more embodiments, the amount of zinc-complexing hydroxyphenylbenzazole compound in solution is about 0.01 nM to about 100 nM. In other embodiments, the amount of zinc-complexing hydroxyphenylbenzazole compound in solution is about 0.1 nM to about 50 nM. In still other embodiments, the amount of zinc-complexing hydroxyphenylbenzazole compound in solution is about 0.2 nM to about 5 nM.

Advantageously, the zinc-complexing hydroxyphenylbenzazole compound when complex to a zinc ion has a fluorescence response emission in the visible region and the near IR region. Thus, when testing for zinc, the fluorescence response emission can be determined in the visible region, the near IR region, or both.

To determine if the zinc-complexing hydroxyphenylbenzazole compound is complexed to zinc, the compound may be excited by being irradiated with radiation having an excitation wavelength. The fluorescence response emission may then be mointired to determine if zinc is present. An excitation wavelength is a wavelength that will excite the hydroxyphenylbenzazole compound causing a fluorescence response to be emitted. In one or more embodiments, the zinc-complexing hydroxyphenylbenzazole compound are excited with an excitation wavelength from about 400 nm to about 550 nm, in other embodiments from about 430 nm to about 500 nm, and in other embodiments about 460 nm.

Upon being radiated with radiation having an excitation wavelength, the zinc complex may emit a fluorescent response. In one or more embodiments, the zinc-complexing hydroxyphenylbenzazole compound that is complexed with a zinc cation has a fluorescence response emission in the near infrared region. In one or more embodiments, the zinc-complexing hydroxyphenylbenzazole compound has a fluorescence response emission in the range of about 700 to about 900 nm, in other embodiments from about 710 to about 800 nm, and in other embodiments about 760 nm.

In one or more embodiments, the zinc-complexing hydroxyphenylbenzazole compound complexed with a zinc cation has a fluorescence response emission in the visible region. In one or more embodiments, the zinc-complexing hydroxyphenylbenzazole compound has a fluorescence response emission in the range of about 500 nm to about 700 nm. In one or more embodiments, the zinc-complexing hydroxyphenylbenzazole compound has a fluorescence response emission in the range of about 530 nm to about 590 nm. In these or other embodiments the zinc-complexing hydroxyphenylbenzazole compound has a fluorescence response emission at about 550 nm.

In one or more embodiments, the uncomplexed zinc-complexing hydroxyphenylbenzazole compound has a fluorescence response emission, when excited, in the range of about 510 to about 570 nm. In one or more embodiments, the uncomplexed zinc-complexing hydroxyphenylbenzazole compound has two fluorescence response emission maxima in the range of about 510 to about 570 nm. In these or other embodiments the zinc-complexing hydroxyphenylbenzazole compound has a fluorescence response emission at about 520 nm and a fluorescence response emission at about 560 nm.

In one or more embodiments, hydroxyphenylbenzazole compound containing a Schiff base moiety may be used for the detection of trivalent metal ions, specifically chromium, aluminium and iron ions. In one or more embodiments, hydroxyphenylbenzazole compound containing a Schiff base moiety for the detection of include a first Schiff base moiety and a second Schiff base moiety situated on the base hydroxyphenylbenzazole group so that they may selectively complex a trivalent metal ion. Hydroxyphenylbenzazole compounds containing a Schiff base moiety that may be used to detect trivalent metal ions may be referred to as trivalent metal complexing hydroxyphenylbenzazole compounds. Advantageously, the trivalent metal complexing hydroxyphenylbenzazole compound can be used to simultaneously detect chromium, aluminium and iron ions in test samples.

Suitable hydroxyphenylbenzazole compounds containing a Schiff base moiety for the detection of trivalent metals include those defined by the formula hydroxyphenylbenzazole compound containing a Schiff base may be defined by the formula IV:

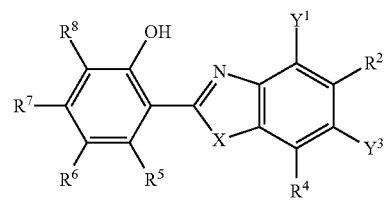

where X is an oxygen atom, a sulfur atom, a nitrogen atom with a pendant hydrogen atom, or a nitrogen atom with a pendant alkyl group; $Y^1$ and $Y^3$ are each individually a Schiff base moiety, and $R^2$, $R^4$, $R^5$, $R^6$, $R^7$, and $R^8$ are each individually a hydrogen atom or a monovalent organic group; and formula V:

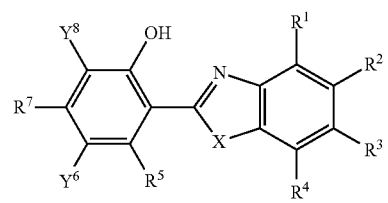

where X is an oxygen atom, a sulfur atom, a nitrogen atom with a pendant hydrogen atom, or a nitrogen atom with a pendant alkyl group; $Y^6$ and $Y^8$ are each individually a Schiff base moiety, and $R^1$, $R^2$, $R^3$, $R^4$, $R^5$, and $R^7$ are each individually a hydrogen atom or a monovalent organic group.

Examples of hydroxyphenylbenzazole compounds containing a Schiff base for the detection of trivalent metals include, but are not limited to

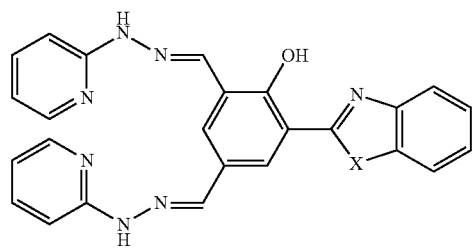

where X is an oxygen atom, a sulfur atom, a nitrogen atom with a pendant hydrogen atom, or a nitrogen atom with a pendant alkyl group;

In one or more embodiments, the trivalent metal complexing hydroxyphenylbenzazole compound may be used to detect the presence of trivalent metal ions in a test sample. The test sample is a substance that may contain trivalent metal ions. The trivalent metal-complexing hydroxyphenylbenzazole compound is contacted with the test sample. An excitation wavelength is then applied to the test sample. In the presence of trivalent metal ions, a trivalent metal complexing hydroxyphenylbenzazole compound will form a complex with a trivalent metal ion, and the complex will give an identifiable emission wavelength or fluorescence response that corresponds to complexed trivalent metal complexing hydroxyphenylbenzazole compound, thus indicating the presence of trivalent metal ions in the test sample. In the absence of trivalent metal ions, no complex will be formed, and the emission wavelength will correspond to the uncomplexed hydroxyphenylbenzazole compound.

The test sample may be obtained directly from a source to be tested for the presence of trivalent metal ions, or it may be created by dissolving or diluting a source in a solvent.

In one or more embodiments, solvents suitable for the creation of test samples include solvents selected from the group consisting of aqueous solvents, protic solvents, organic solvents, and mixtures thereof. Examples of aqueous solvents include, but are not limited to, water and pH buffered solutions. Examples of protic solvents include, but are not limited to, lower alcohols, such as methanol and ethanol. Examples of organic solvents include, but are not limited to, tetrahydrofuran and methylene chloride.

Similarly to the zinc-complexing hydroxyphenylbenzazole compound, this method can be used to test a large number of test samples all at the same time. However, advantageously, the trivalent metal-complexing hydroxyphenylbenzazole compound may be used to test for multiple metals at the same time. This is again shown in FIG. 1, showing a method 10, wherein a light source 12 directs light 30 (a stimulated emission of photons) through a first container 14 holding a test sample 16, a second container 18 holding a test sample 20 and a third container 22 holding a test sample 24. As seen, the first container 14 and third container 28 hold test samples 16 that include a trivalent metal, because the light 30 causes fluorescence whose color can be seen visually as at 26 (container 14) and 28 (container 22). Advantageously, 26 and 28 may show the presence of different metals. Or examples 26 may be aluminum, while 28 is chromium. The second container 18 does not show fluorescence and thus, the test sample 20 placed therein does not include trivalent metal.

The test sample may comprise or include living or dead cells from an organism, or an entire living organism or a portion of an organism that includes living or dead cells. In one or more embodiments, the trivalent metal complexing hydroxyphenylbenzazole compound may be used to detect the presence of trivalent metal ions in vivo, by testing an entire living organism or a portion of an organism that contains living cells for the presence of trivalent metal ions.

The trivalent metal complexing hydroxyphenylbenzazole compound may be added in vivo, by contacting living cells with a trivalent metal complexing hydroxyphenylbenzazole compound. In one or more embodiments, the living cells that are contacted by the trivalent metal complexing hydroxyphenylbenzazole compound are tissues or part of a living organism. Examples of methods of contacting living cells with a trivalent metal complexing hydroxyphenylbenzazole compound include, but are not limited to, incubating cultured cells with the trivalent metal complexing hydroxyphenylbenzazole compound in a culture medium, and injecting trivalent metal complexing hydroxyphenylbenzazole compound into living cells. Examples of methods of contacting a living organism with a trivalent metal complexing hydroxyphenylbenzazole compound include, but are not limited to, treating a portion of water containing an aquatic animal with a trivalent metal complexing hydroxyphenylbenzazole compound. Other methods of contacting a living organism with a trivalent metal complexing hydroxyphenylbenzazole compound include, but are not limited, ingestion and injection.

In one or more embodiment, the presence of trivalent metal ions in vivo may be found by exciting the living cells or living organism with an excitation wavelength. If zinc ions are present in vivo the trivalent metal complexing hydroxyphenylbenzazole compound will form a complex with a zinc ion and the trivalent metal complexing hydroxyphenylbenzazole compound will give an emission wavelength, or fluorescence response, corresponding to complexed trivalent metal complexing hydroxyphenylbenzazole compound and the presence of trivalent metal ions will be detected. In the absence of trivalent metal ions, the trivalent metal complexing hydroxyphenylbenzazole compound will not form a complex and the trivalent metal complexing hydroxyphenylbenzazole compound will give an emission wavelength corresponding to uncomplexed trivalent metal complexing hydroxyphenylbenzazole compound.

The amount of trivalent metal complexing hydroxyphenylbenzazole compound used to detect trivalent metal ions can also be defined in terms of micromolar (μM) to nanomolar range. In one or more embodiments, the amount of trivalent metal complexing hydroxyphenylbenzazole compound in solution is 0.01 nM to 100 μM. In other embodiments, the amount of trivalent metal complexing hydroxyphenylbenzazole compound in solution is 10 nM to 50 μM. In still other embodiments, the amount of trivalent metal complexing hydroxyphenylbenzazole compound in solution is 10 nM to 10 μM.

To determine if the trivalent metal complexing hydroxyphenylbenzazole compound is complexed to a trivalent metal, the compound may be excited by being irradiated with radiation having an excitation wavelength. In one or more embodiments, the trivalent metal complexing hydroxyphenylbenzazole compound are excited with an excitation wavelength in the range from about 300 nm to about 450 nm, in other embodiments about 350 nm to about 430 nm, and in still other embodiments about 390 nm to about 410 nm.

Upon being radiated with radiation having an excitation wavelength, the trivalent metal complexing hydroxyphenylbenzazole compound may emit a fluorescent response. In one or more embodiments, the trivalent metal complexing hydroxyphenylbenzazole compound will exhibit a fluorescence response emission in the visible region when excited.

In one or more embodiments, the trivalent metal complexing hydroxyphenylbenzazole compound complexed with a chromium cation has a fluorescence turn-on response with emission in the range of about 500 nm to about 610 nm, in other embodiments about 530 nm to about 580 nm, and in still other embodiments about 550 nm to about 570 nm.

In one or more embodiments, the trivalent metal complexing hydroxyphenylbenzazole compound complexed with an aluminum cation has a fluorescence turn-on response with emission in the range of about 470 nm to about 580 nm, in other embodiments about 500 nm to about 550 nm, and in still other embodiments about 520 nm to about 540 nm.

In one or more embodiments, the trivalent metal complexing hydroxyphenylbenzazole compound complexed with an iron cation has an immediate fluorescence turn-on, whose fluorescence intensity fades gradually. In one or more embodiments, the fluorescence response fades within 5 minutes. The observation of the fluorescence turn-on, followed by quick signal fading, can be used to differentiate iron from other trivalent cations. The fluorescence turn-on emission for iron in the range of about 500 nm to about 610 nm, in other embodiments about 530 nm to about 580 nm, and in still other embodiments about 550 nm to about 570 nm.

While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

EXAMPLES

Zinc-Complexing Hydroxyphenylbenzazole Compounds

A bis(HBO) 3-Zn has been designed by changing the $R_1$ and $R_2$ substituents in 1-Zn to respective benzoxazole and hydroxy groups to introduce the $2^{nd}$ HBO. Upon binding to $Zn^{2+}$ cation, the weak fluorescence of 3 is turned on, giving both green ($\lambda_{em} \approx 540$ nm) and NIR emission ($\lambda_{em} \approx 750$ nm). The NIR turn-on signal from 3, however, also responds to $Cd^{2+}$ cation. It remains a challenge to develop a $Zn^{2+}$ sensor that gives desirable NIR emission without interfering from the structurally similar $Cd^{2+}$ cation. In addition, the intensity of the desirable NIR emission from 3-Zn also needs to be further tuned. And the synthesis of the sensor needs to be simplified for practical applications.

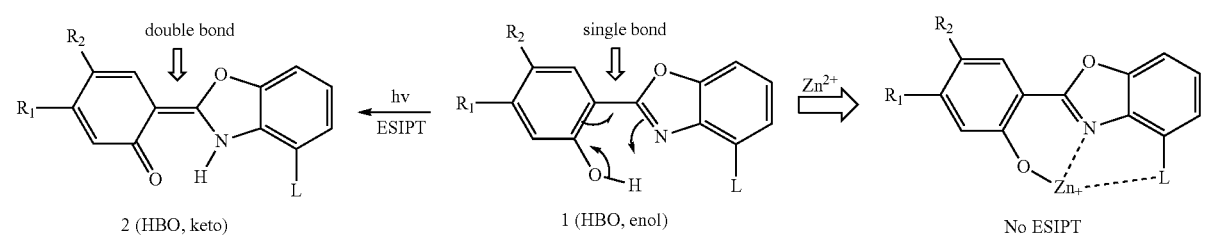

Scheme 1. Structures of 2-(2'-hydroxyphenyl) benzoxazole. $R^1$ is a hydrogen atom or a monovalent organinic group, and $R_1$ and $R_2$ are defined as in scheme 1.

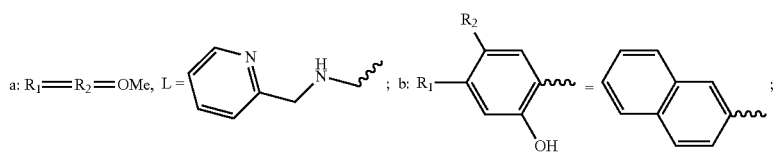

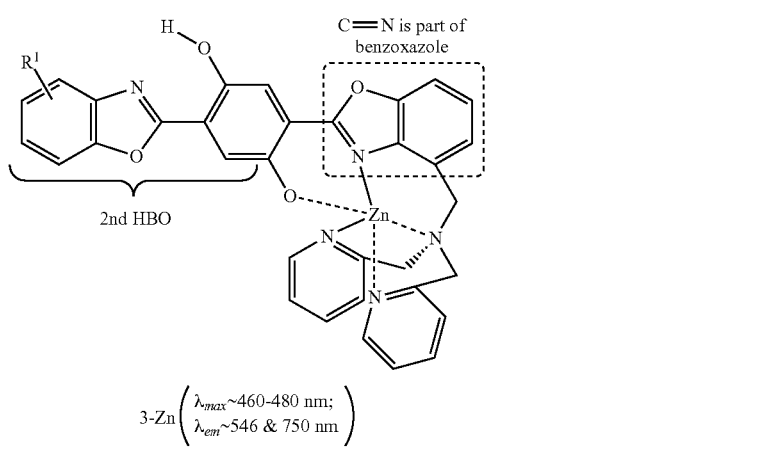

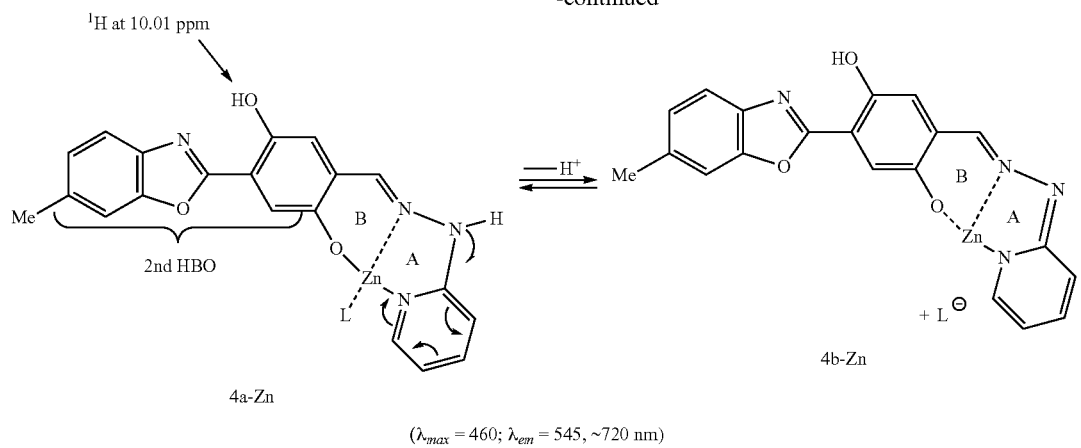

($\lambda_{max} = 460$; $\lambda_{em} = 545$, ~720 nm)

In an effort to tune the performance of the ESIPT probe, the complex 4-Zn was prepared. In comparison with 3-Zn, the complex 4-Zn uses an isolated imine bond (—CH=N—) to bind $Zn^{2+}$ cation. When the zinc-binding benzoxazole fragment in 3 is replaced by a —CH=N— bond, one of two HBO units in bi(HBO) 3 is removed, which is believed to influence the ESIPT signal of the neutral ligand and its metal complexes. In addition, the zinc-chelation of 4 will form a more stable five-membered ring "A" involving the —CH=N— and pyridyl groups, in contrast to a six-membered ring in 3-Zn that involves the benzoxazole and pyridyl groups. Such structural change is believed to perturb the interaction between the zinc cation and phenolic oxygen, thereby tuning the ESIPT of the second HBO unit.

While some Schiff-base chemosensors are known for selective $Zn^{2+}$ detection, they give fluorescence either in the blue or green colors with small Stokes' shift (~30 nm). In addition, the known Shiff-base sensors are dependent on the fluorescence turn-on through metal binding-induced isomerization of —C=N— bond with little spectral shift. Advantageously, the mono HBO sensor 4 improves the selectivity of $Zn^{2+}$ binding. Intriguingly, the sensor 4 exhibited great selectivity toward $Zn^{2+}$ binding, which turns on the ESIPT to give the desirable NIR emission (at ~720 nm) with a large Stokes' shift (~260 nm). The findings demonstrate that a Schiff base can serve as an effective switch for the ESIPT turn-on, whose excellent selectivity to bind zinc cation makes the NIR sensor an attractive candidate for practical applications.

TABLE 1

| | Absorption $\lambda_{max}$ (nm) | Emission $\lambda_{em}$ (nm) | Stokes' shift |
|---|---|---|---|
| 1a | 337 | 407 | 5103 cm$^{-1}$ (70 nm) |
| 1a-Zn | 376 | 443 | 4022 cm$^{-1}$ (67 nm) |
| 1b | 379 | 550 | 8203 cm$^{-1}$ (171 nm) |
| 1b-Zn | 443 | 542 | 4123 cm$^{-1}$ (99 nm) |
| 3 | 412 | 456, 610*,11 | 7878 cm$^{-1}$ (198 nm) |
| 3-Zn | 465 | 546, 750* | 8172 cm$^{-1}$ (285 nm) |
| 4 | 413 | 580 | 6971 cm$^{-1}$ (167 nm) |
| 4-Zn | 450 | 545, 720* | 8333 cm$^{-1}$ (270 nm) |

Synthesis of 4 was accomplished by reaction of 2-hydrozinylpyridine with the corresponding aldehyde 6 in high yield (Scheme 2). The simplicity in the synthesis of the ligand 4 was in sharp contrast to that of ligand 3 which used a sequence of four synthetic steps from the aldehyde (with low yield).

Figure 2:
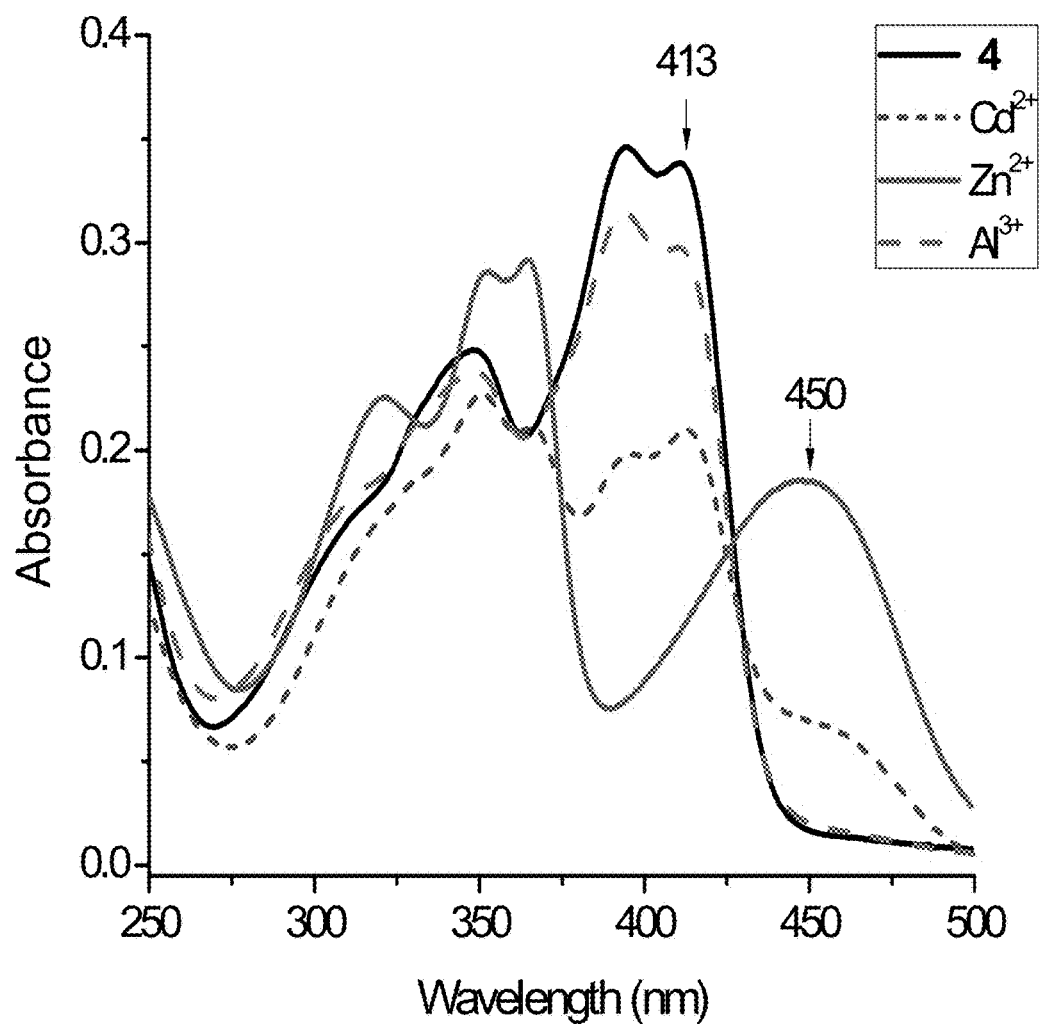
FIG. 2 provides an absorbance spectra of 4 (10 μM) in EtOH/HEPES (10 mM) (1:1) (pH=7.2), upon addition of 5 equiv. of different cations.

The binding property of 4 to $Zn^{2+}$ cation was examined in EtOH/HEPES (FIG. 2). As the $Zn^{2+}$ cation was added, a new absorption band was generated at about 450 nm. The new band was attributed to the removal of a phenolic proton as shown in 4-Zn complex. The signal change appeared to be complete when one equivalent $Zn^{2+}$ was added, suggesting a 1:1 ligand-to-metal ratio. Addition of other cations, such as $Al^{3+}$, however, did not cause a notable bathochromic shift, indicating that their bindings were not sufficiently strong to remove the phenolic proton (FIG. 2). The sensor also showed weak binding to $Cd^{2+}$ cation.

Scheme 2. Synthesis of sensor 4

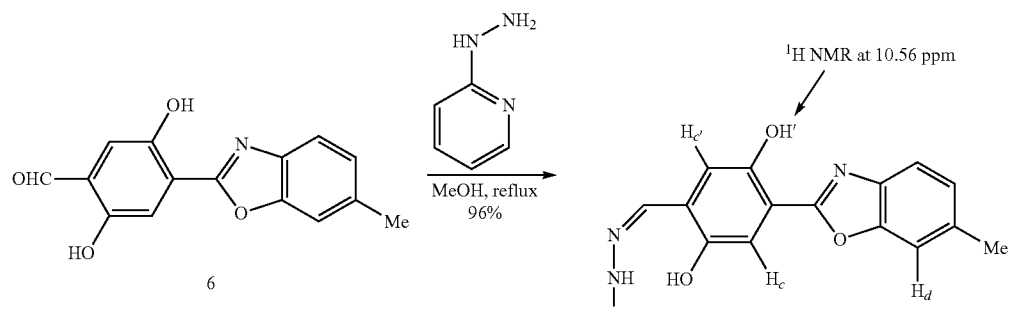

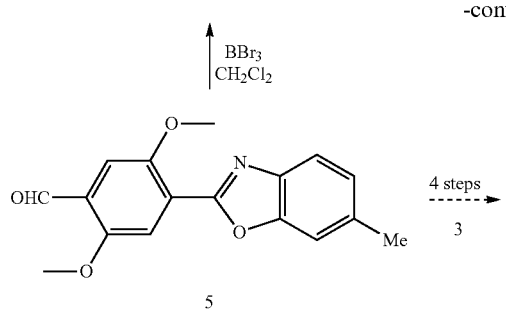 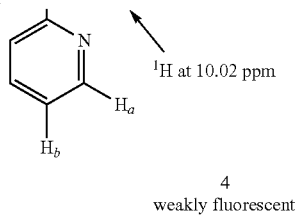

4 steps 4
weakly fluorescent

Figure 3:
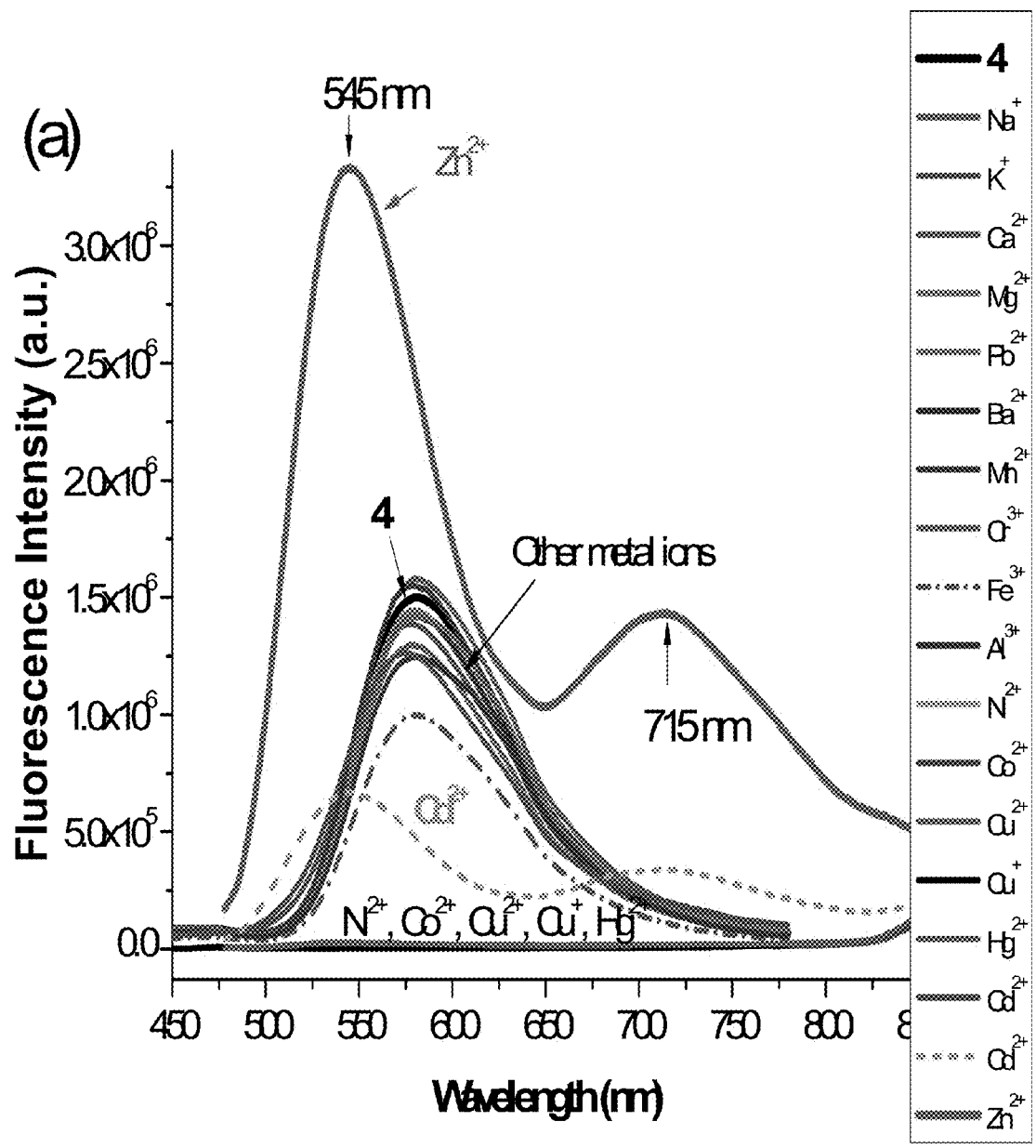
FIG. 3 provides a fluorescence spectra of 4 (10 μM) in EtOH:HEPES=1:1 (pH=7.2) upon addition of 5 equiv. of different ions.

The ligand 4 gave a weak fluorescence peak at 580 nm ($\varphi_{fl}$=0.05). Upon addition of $Zn^{2+}$ cation, the fluorescence was significantly increased ($\varphi_{fl}$=0.26 in 1:1 EtOH/$H_2O$), giving two new emission peaks at 545 and ~720 nm (FIG. 3), which corresponds to the emission from the enol and keto tautomers of 4-Zn, respectively. NIR emission was relatively stronger in pure methanol. The green fluorescence turn-on could be easily observed, making it also useful for naked eye detection (FIG. 3). Interestingly, addition of other cations ($K^+$, $Na^+$, $Ag^+$, $Cd^{2+}$, $Ca^{2+}$, $Mg^{2+}$, $Pb^{2+}$, $Ni^{2+}$, $Hg^{2+}$, $Co^{2+}$, $Cu^{2+}$, $Cr^{3+}$, $Fe^{3+}$, $Al^{3+}$) to 4 did not induce the dual emissions at 545 and 720 nm. In other words, the probe molecule 4 is silent to $Cd^{2+}$ cation, as its binding could not remove the phenolic proton (a necessary step to simultaneously shift the emission and turn on the ESIPT for NIR emission). The $Al^{3+}$ cation only induced an enhanced emission at ~610 nm, as its stronger Lewis acid character could lead to a moderately strong interaction with the phenol segment. In summary, the sensor 4 displayed an excellent selectivity toward $Zn^{2+}$ binding, which simultaneously induced both fluorescence turn-on and a large spectral shift.

Figure 5:
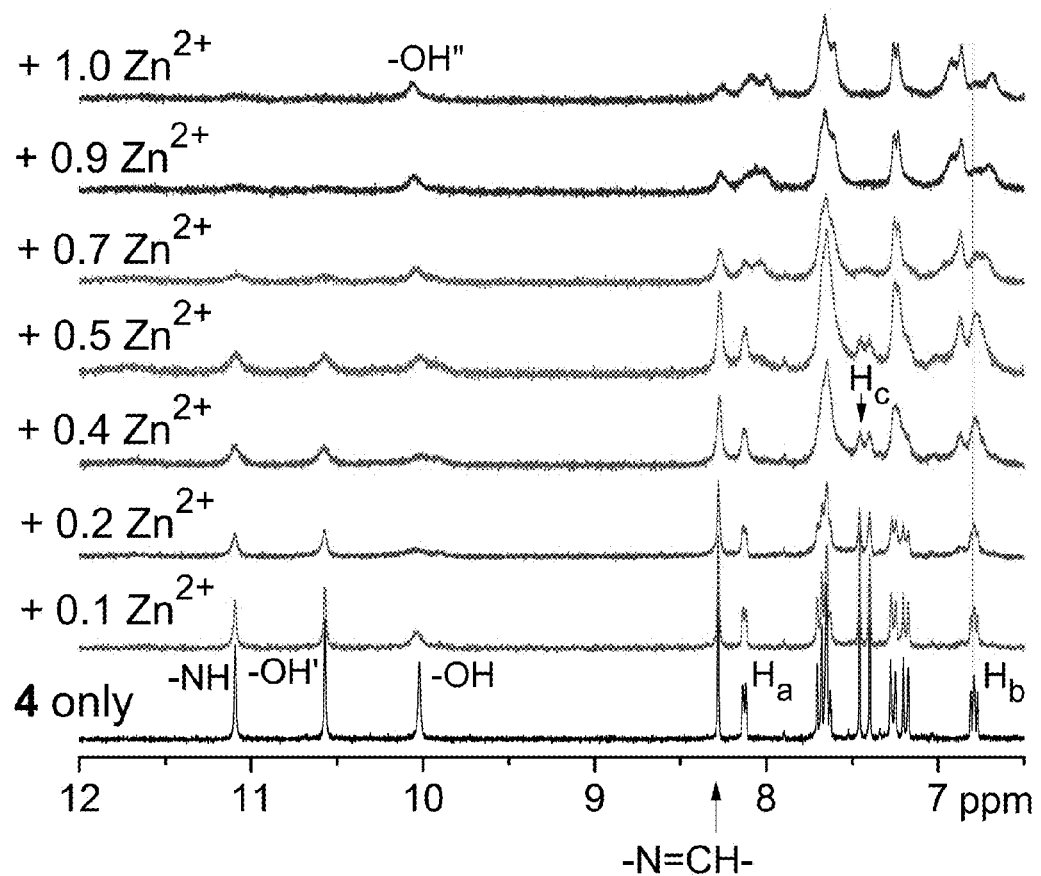
FIG. 5 provides a chart of $^1$H NMR titration of 4 with $Zn(OAc)_2$ in DMSO-$d_6$; Disappearance of signal $H_c$ at ~7.38 ppm supports the 1:1 ligand-to-metal ratio.
Figure 6:
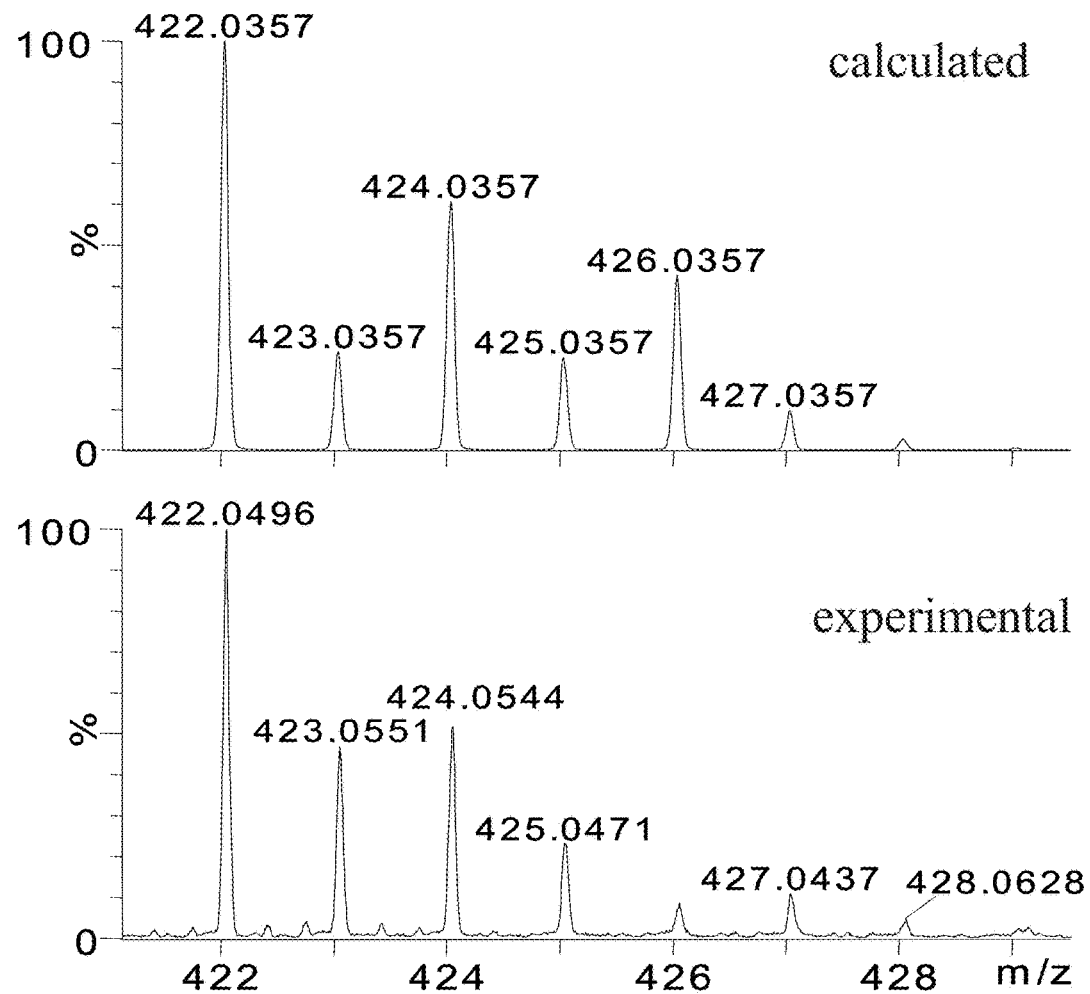
FIG. 6 provides a mass spectrum of 4-Zn (Calcd for $C_{20}H_{14}N_4O_3Zn$ 422.0357).

In the $^1H$ NMR of ligand 4 (FIG. 5), the signals at 10.56 and 10.02 ppm were attributed to the phenolic protons (—OH' and —OH, respectively), while the signals at 11.09 ppm was assigned to the amine Upon addition of $Zn^{2+}$ (one equiv), the —OH' at 10.56 ppm was transformed to —OH" (at ~10 ppm), as a consequence of forming 4-Zn. The unusually broad signals at ~10 ppm, when 0.2-0.5 equiv of $Zn^{2+}$ was added, were partially attributed to the presence of both —OH (in 4) and —OH" (in 4-Zn). Two singlet Ar—H signals ($H_c$ or $H_{c'}$ at 7.38, and $H_d$ at 7.44 ppm) were gradually decreased with addition of $Zn^{2+}$, in agreement with the large electronic impact associated with the formation of metal complex. It should be noted that the 2-(hydrozino)pyridine unit in 4a-Zn can be tautomerized to give 4b-Zn (Scheme 1), which might also contribute to the signal broadening from the $^1H$ NMR. Mass spectrometry detected m/z=422.0496 by HRMS (FIG. 6), corresponding to [4b-Zn-L] (calcd for $C_{20}H_{14}N_4O_3Zn$: 422.0357).

In order to clarify the interaction of 4 with different metal ions, the UV-vis absorption and fluorescence spectra of 4 (10 µM in EtOH:$H_2O$=1:1 solutions) were studied by addition of 5 equiv. of different cations. In addition to no response to physiologically important $K^+$, $Na^+$, $Ca^{2+}$ ions, the sensor also exhibited no observable fluorescence response to $Cd^{2+}$ cation, which led to greatly improved selectivity over the previous sensor 3. While some cations ($Ag^+$, $Co^{2+}$, $Ni^{2+}$ and $Cu^{2+}$) quenched the fluorescence, addition of $Cr^{3+}$, $Fe^{3+}$ and $Al^{3+}$ cations slightly increased the fluorescence whose signals were red-shifted by ~25-37 nm. Only $Zn^{2+}$ binding gave enhanced emissions at 545 nm and ~720 nm, which are significantly shifted from the neutral ligand (580 nm) to allow the positive identification of the zinc cation.

Figure 4:
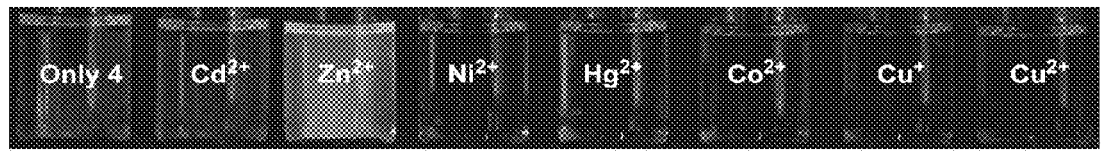
FIG. 4 provides fluorescent images after addition of different metal ions to 4 (10 μM in EtOH:HEPES=1:1).

As revealed from FIGS. 3 and 4, only zinc binding to 4 could effectively turn on the ESIPT, giving enhanced emission from both enol ($\lambda_{em}\approx545$ nm) and keto tautomers ($\lambda_{em}\approx720$ nm). A It is important to note that, while the ligand 4 can bind $Zn^{2+}$ cation well, the same is not true for the $Cd^{2+}$ cation, although the atomic configuration ([Ar]$3d^{10}$ for $Zn^{2+}$ and [Kr]$4d^{10}$ for $Cd^{2+}$). On the basis of quick disappearance of the —OH signal at ~10 ppm ($^1H$ NMR in FIG. 5), the initial step might involve a weak interaction of metal cation with the imine —CH=N—, forming intermediate 5. Interaction with the pyridyl then led to a more stable 5-membered ring "A" as shown in 6. The $Zn^{2+}$ cation in 6a could further interact with the adjacent hydroxyl group to form the fused 6-membered ring "B", which requires twisting of the "HBO" fragment from the Schiff base fragment (ring A). The intermediate 7 could quickly lose a proton to give 4-Zn, which is detected in the absorption spectrum. From the fluorescence titration data, the association constant was determined to be $K_a$=2.28×$10^5$ $M^{-1}$.

Scheme 3. Possible formation of $Zn^{2+}$ and $Cd^{2+}$ complexes. $R^1$ is a hydrogen atom or a monovalent organic group.

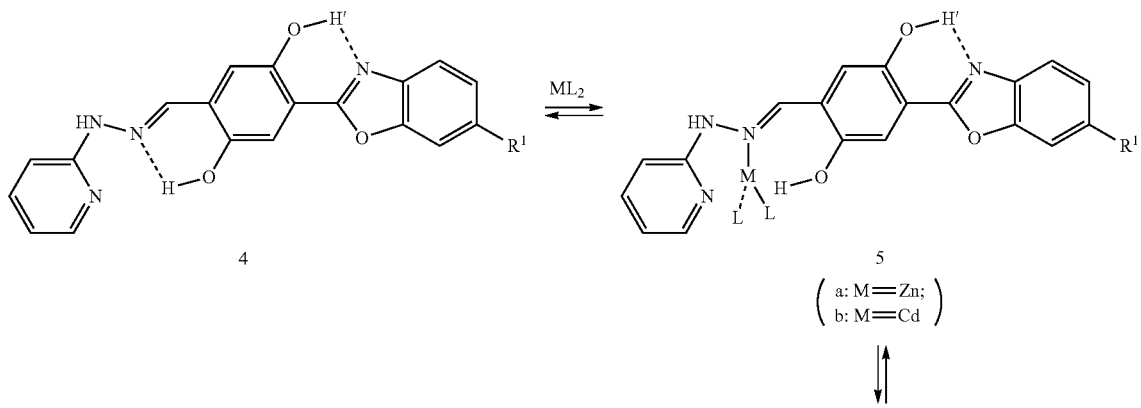

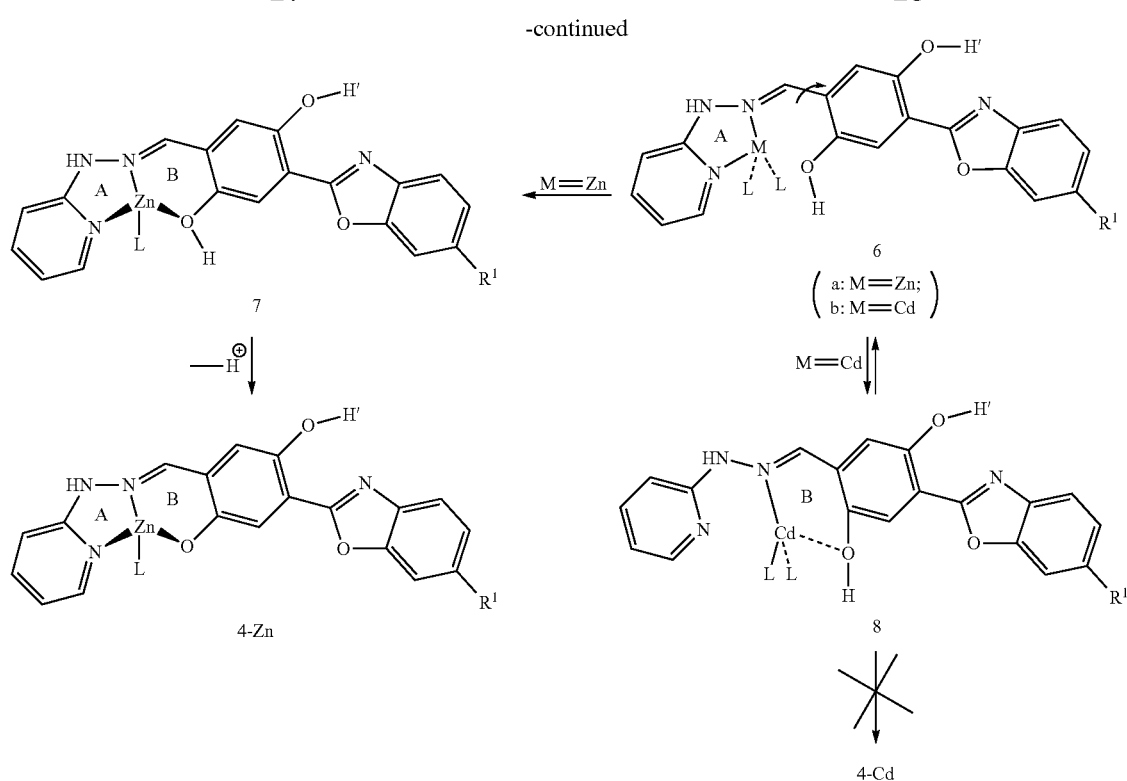

When Cd$^{2+}$ was used, the interaction pattern appeared to be quite different. The $^1$H NMR titration using Cd$^{2+}$ revealed that the pyridyl protons H$_a$ and H$_b$ were not affected after addition of one equiv of Cd$^{2+}$ cation, indicating the lack of tight and stable binding to pyridyl ring. Therefore, the equilibrium between 6b and 8 might occur without forming the fused rings A-B in 4-Cd. This might be due to the larger size of Cd$^{2+}$ cation (or longer Cd—N & Cd—O bonds), which destabilizes the fused A-B rings in 4-Cd as observed from a molecular modeling comparison. The proposed fast equilibrium between 6b and 8 accounts for the experiment findings: (a) addition of Cd$^{2+}$ cation induced a smaller peak of bathochromic shift in the absorption spectrum of 4 (FIG. 2), indicating the weak binding of Cd$^{2+}$ cation to phenol (without removing phenolic proton); (b) disappearance of phenolic protons in $^1$H NMR. Although the strength of lewis acid (Zn$^{2+}$>Cd$^{2+}$) could play a role in their differentiation, Lewis acidity alone could not explain the lack of formation of 4-Cd under the experimental conditions.

Figure 7:
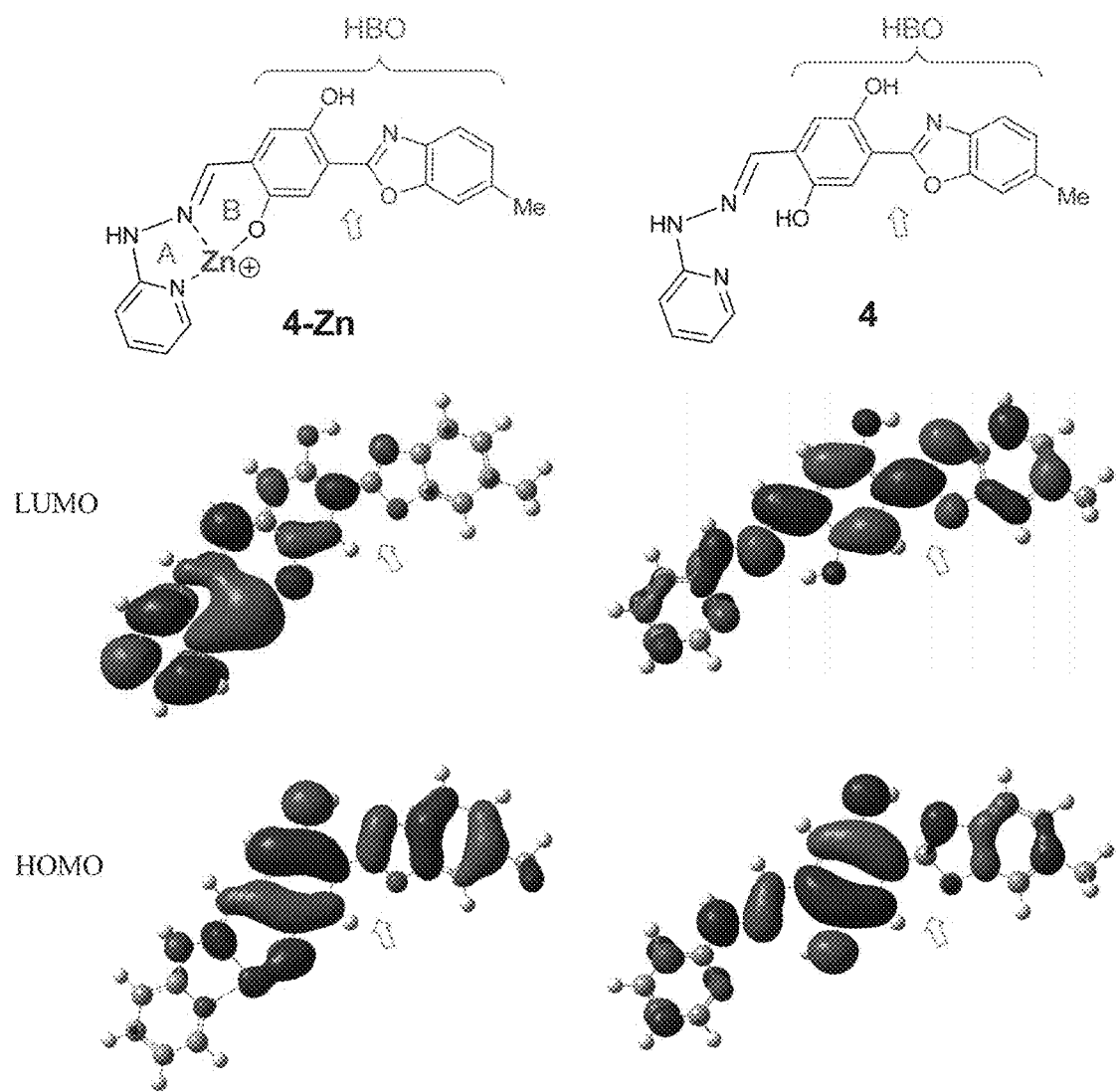
FIG. 7 provides a map of the HOMO and LUMO orbitals of 4-Zn and 4, calculated with DFT at the B3LYP/6-31G level using Gaussian 09. The double arrows indicate the orbital lobes between the phenol and benzoxazole fragments.

In the zinc-sensing process, the zinc-binding in 4-Zn advantageously affects the ESIPT event in HBO, in comparison with the ligand 4. As shown in 1→2 (Scheme 1), the ESIPT event in HBO is dependent on the electronic connection between the phenol and benzoxazole fragments. Computation with DFT at the B3LYP/6-31G level revealed that the LUMO of HBO in 4 had a large orbital interaction between the phenol and benzoxazole fragments (FIG. 7), which could facilitate the proton transfer in the excited state. The calculation was consistent with the experimental finding that the ligand 4 gave only ESIPT emission, indicating the important role of the electronic connection in the LUMO of HBO. The calculation further revealed that the electronic connection between the phenol and benzoxazole fragments became weaker in the LUMO of 4-Zn, which might be responsible for partial conversion of the excited 4-Zn (the enol tautomer) to its keto tautomer. This led to emission from both enol and keto tautomers of 4-Zn. In other words, the new zinc sensor exhibited several attractive features: (1) using Schiff base binding to weaken ESIPT emission to reduce the background emission signal; Lack of enol emission from 4 is also an improved feature over the previous sensor 3.[11] (2) introducing zinc binding to induce a large spectral shift for emission in NIR region; (3) using zinc binding to perturb the electronic linkage to attenuate the ESIPT, thereby allowing dual emission.

Figures 8A, 8B:
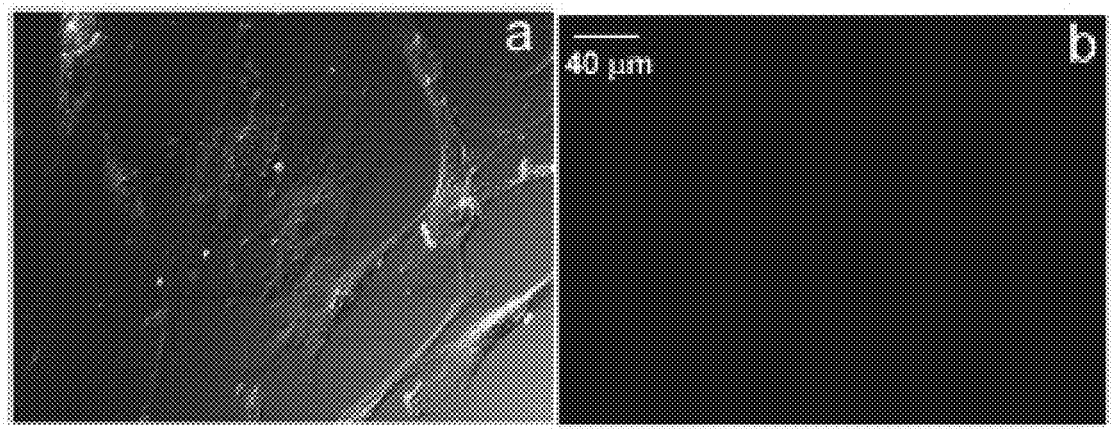
FIG. 8A provides confocal fluorescence images of Human mesenchymal stem cells (hMSCs) excited with a 488 laser. The image were collected at bright field on an Olympus FV1000-Filter Confocal Microscopy. a→b: the cells were incubated with dye 4 for 60 mins at 37° C.
FIG. 8B provides confocal fluorescence images of Human mesenchymal stem cells (hMSCs) excited with a 488 laser. The images were collected at green channel (535-565 nm) on an Olympus FV1000-Filter Confocal Microscopy. a→b: the cells were incubated with dye 4 for 60 mins at 37° C.
Figures 8C, 8D:
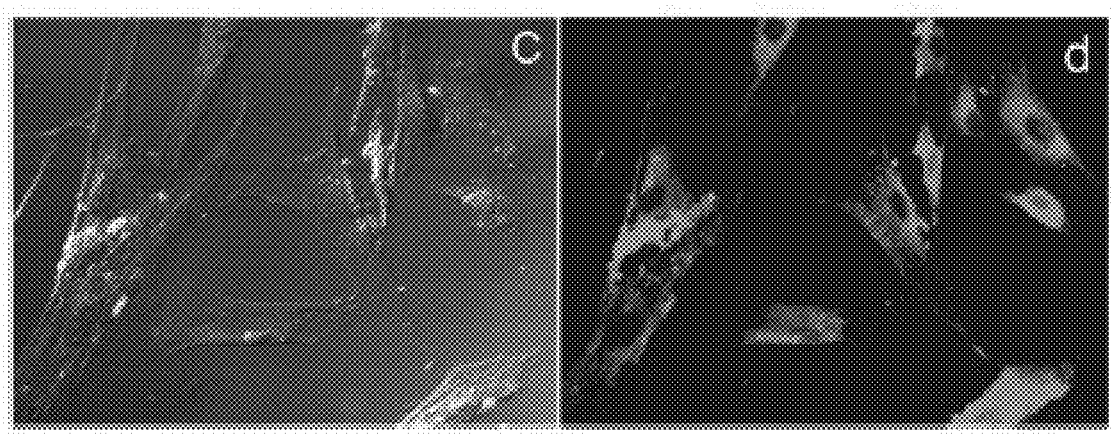
FIG. 8C provides confocal fluorescence images of Human mesenchymal stem cells (hMSCs) excited with a 488 laser. The images were collected at bright field on an Olympus FV1000-Filter Confocal Microscopy. c→d: the cells were first treated with $Zn(OAc)_2$ (30 μM) for 30 mins and further exposed to dye 4 (10 μM) for another 60 mins at 37° C.
FIG. 8D provides confocal fluorescence images of Human mesenchymal stem cells (hMSCs) excited with a 488 laser. The images were collected green channel (535-565 nm) on an Olympus FV1000-Filter Confocal Microscopy. the cells were first treated with $Zn(OAc)_2$ (30 μM) for 30 mins and further exposed to dye 4 (10 μM) for another 60 mins at 37° C.
Figure 9:
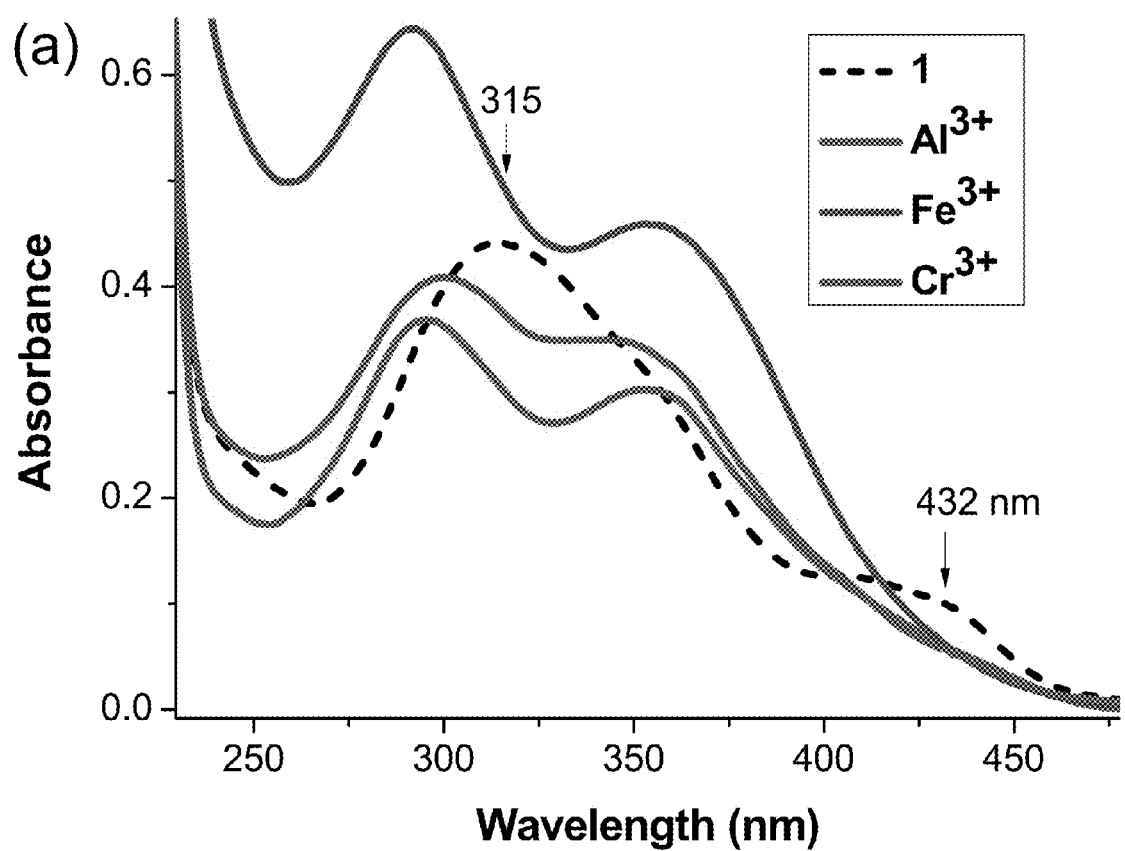
FIG. 9 provides a UV-vis chart of 1 upon addition of 10 equiv of different metal ions in aqueous (8:2=water:EtOH.
Figure 10:
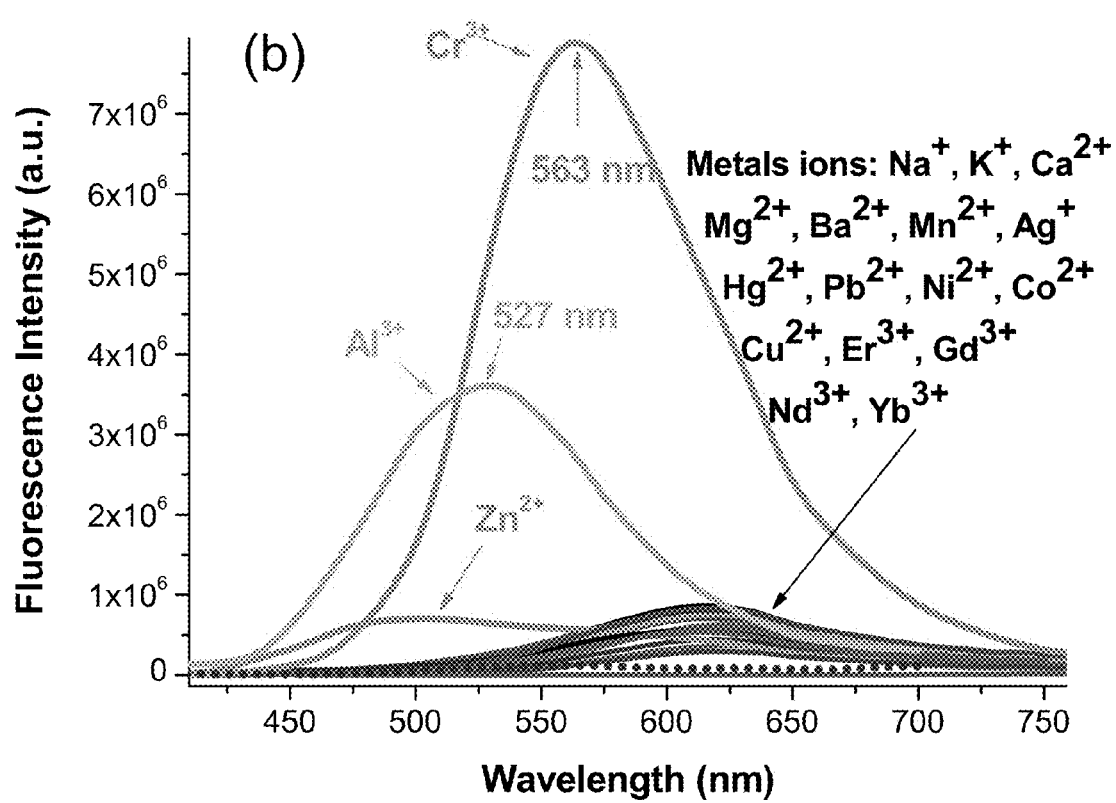
FIG. 10 provides fluorescence response chart of 1 upon addition of 10 equiv of different metal ions in aqueous (8:2=water:EtOH.

To illustrate the potential biological application, sensor 4 was applied to visualize intracellular Zn$^{2+}$ in both human cancer cells (HepG2) and human umbilical vein endothelial cells (HUVECs) (See FIGS. 8A-D). FIGS. 8A-D show confocal fluorescence images of Human mesenchymal stem cells (hMSCs) excited with a 488 laser. The images were collected at bright field (a and c) and green channel (535-565 nm; b and d) on an Olympus FV1000-Filter Confocal Microscopy. a→b: the cells were incubated with dye 4 for 60 mins at 37° C.; c→d: the cells were first treated with Zn(OAc)2 (30 μM) for 30 mins and further exposed to dye 4 (10 μM) for another 60 mins at 37° C. For this purpose, cells were first incubated with 30 μM of Zn$^{2+}$ for 30 mins and then further treated with 10 μM dye 4 for another 30 mins before imaging. While very weak fluorescence was observed in cells treated with only dye 4 (FIG. 8b), strong fluorescence was observed from both cell lines which are treated with both Zn$^{2+}$ and dye 4 (FIG. 8d). These results demonstrate that the probe is permeable to cells, binds to intracellular Zn$^{2+}$, and emits strong fluorescent light upon binding to the metal ion. Thus the probe is highly suitable for determining intracellular Zn$^{2+}$.

A cell permeable sensor which is highly selective (almost specific) for zinc cation has been demonstrated. The sensor design successfully utilizes the Schiff base in the zinc-binding event, which subsequently induces the ESIPT of HBO 4 to produce a large fluorescence response. In contrast to the existing sensors that typically give one signal, the new sensor generates not only a large fluorescence turn-on at ~545 nm but also the desirable NIR emission (~720 nm) with a large Stokes' shift. Since only the zinc bonding can induce the ESIPT, the sensor can be used for reliable monitoring of $Zn^{2+}$ concentration. The metal binding studies also reveal that the specific zinc response could be attributed to the sensor's ability to form the fused A-B rings with $Zn^{2+}$ (as shown in 4-Zn). The strict binding requirement associated with the fused A-B rings makes the sensor silent to $Cd^{2+}$, whose interference often poses a challenge in $Zn^{2+}$ detection. This could be due to the combination of the following reasons: (1) weak binding of $Cd^{2+}$ to 4 (FIG. 2), as cation's relative large size destabilizes the fused A-B rings; (2) fluorescence quenching minimizes its interference (FIGS. 3 and 4).

Trivalent Metal Complexing Hydroxyphenylbenzazole Compounds

The sensor design incorporates a 2-(2'-hydroxyphenyl) benzoxazole (HBO) unit as an emitting fluorophore, whose emission has a large Stokes' shift (>150 nm) arising from the excited-state intramolecular proton transfer (ESIPT). The sensor enables simultaneous detection $Cr^{3+}$, $Al^{3+}$ and $Fe^{3+}$ ions, by naked eyes, in aqueous solution. As shown in scheme 4, the cation binding is believed to occur by using two stronger ligands 2-(pyridin-2'-yl)hydrozono groups (2). Due to steric hindrance with $H_a$ atom, the C=N will be twisted away from the coplanarity (with HBO) upon binding metal cations. It is assumed that only those metal cations that can bind strongly with the imine bonds will be able to compete, thus separating the trivalent cations from the divalent and monovalent ones. The design does not require the participation of a phenol group in the cation binding event, thereby preserving the phenolic proton to maintain the ESIPT property. Also, the trivalent cations can be differentiated, since the ESIPT of HBO unit is quite sensitive to electronic perturbation from the cation binding.

for 2 hours, and was collected as yellow solid in >90% yield. The absorption of 1 revealed a major peak (at 315 nm, attributed to $\pi$-$\pi$*) and a minor peak (at 432 nm, attributed to n-$\pi$*).

Figure 11:
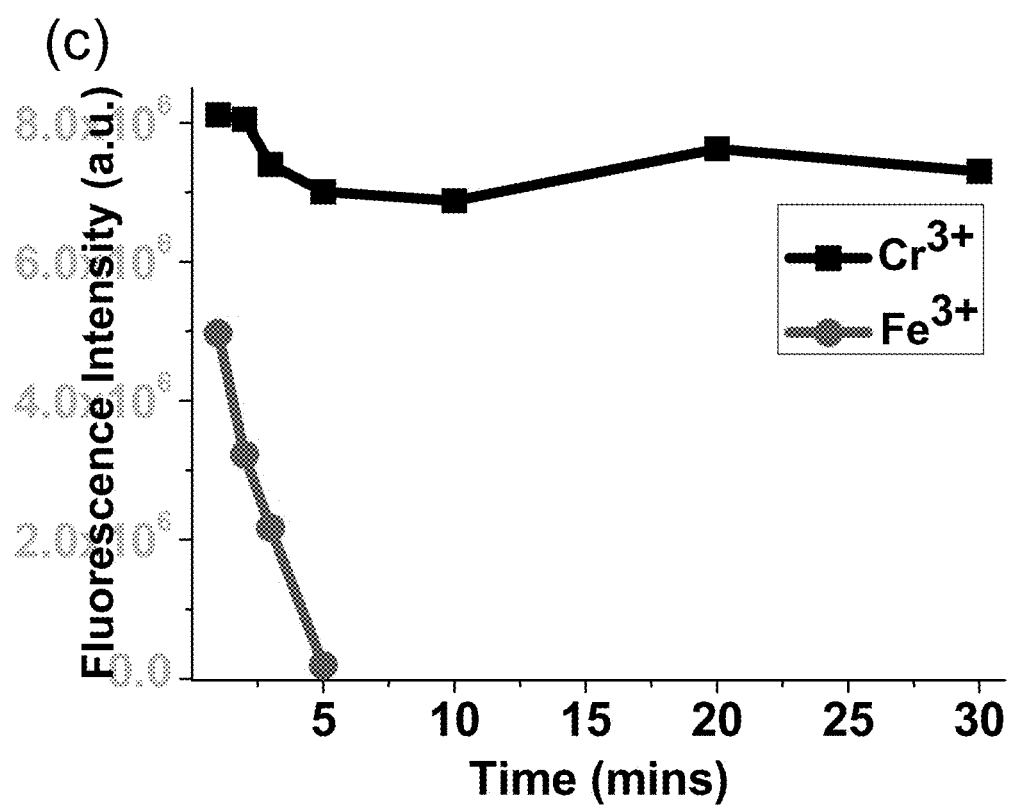
FIG. 11 provides a chart of the fluorescence change of 1 upon addition of $Fe^{3+}$ and $Cr^{3+}$ over time upon addition of 10 equiv of different metal ions in aqueous (8:2=water: EtOH).
Figure 12:
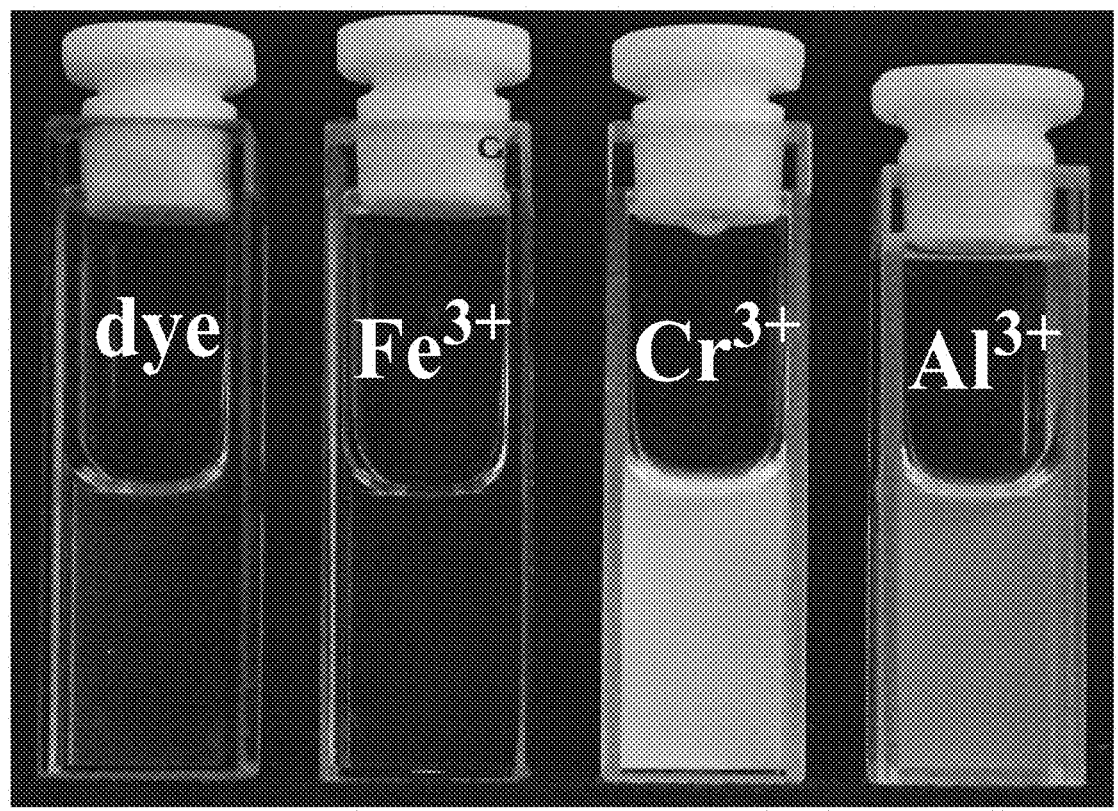
FIG. 12 provides an image of the fluorescence response of 1 and 1 upon addition of 10 equiv of different metal ions in aqueous.

The fluorescence response of 1 was examined in aqueous medium ($H_2O$:EtOH=8:2) by addition of various metal ions. Sensor 1 showed weak red fluorescence ($\Phi_F$=0.1) with a large Stokes' shift (180 nm), attributing to emission from its keto tautomer associated with its ESIPT property. Only negligible fluorescence change was observed by addition of 10 equivalents. of the divalent metal ions (except $Cu^{2+}$ quenched the fluorescence). Surprisingly, fluorescent intensity of 1 showed immediate fluorescence turn-on upon addition of trivalent ions $Cr^{3+}$, $Al^{3+}$ and $Fe^{3+}$, although $Cr^{3+}$ and $Fe^{3+}$ are widely known as fluorescent quenchers. Interestingly, the sample with $Fe^{3+}$ quenched the fluorescence quickly within 5 minutes, while the fluorescence with $Cr^{3+}$ and $Al^{3+}$ complexes was quite stable (See FIG. 11). This difference in optical response allows $Fe^{3+}$ (which quenches fluorescence) from $Cr^{3+}$ (emission $\lambda_{em}$~556 nm, yellow green) and $Al^{3+}$ ($\lambda_{em}$~527 nm, blue-green). In summary, different response to trivalent ions enabled the naked eyed detection of $Cr^{3+}$, $Fe^{3+}$ and $Al^{3+}$ cations. (Cr: $\Phi_F$=0.63; Al: $\Phi_F$=0.31).

To elucidate the metal binding model, the UV-vis spectra of 1 were recorded upon addition of different equivilents of $Cr^{3+}$. As is known, the deprotonation of the phenol upon metal binding will lead to large spectral bathochromic shift together with fluorescence blue shift, resulting in a smaller Stokes' shift. Upon addition of $Cr^{3+}$, the absorption band at 432 nm (n-$\pi$*) progressively decreased, indicating that the cation was binding to the Schiff base. The new $\pi$-$\pi$* absorption band was observed at about 358 nm. It should be noted that the emission of the metal complex exhibited a large Stokes' shift (195 nm for $Cr^{3+}$ and 170 for $Al^{3+}$ respectively), which indicates the existence of the free phenol group and ruled out the binding mode 3. All these facts pointed to formation of the metal complex 2, where $Al^{3+}$ and $Fe^{3+}$ showed the similar binding mode. To further prove the

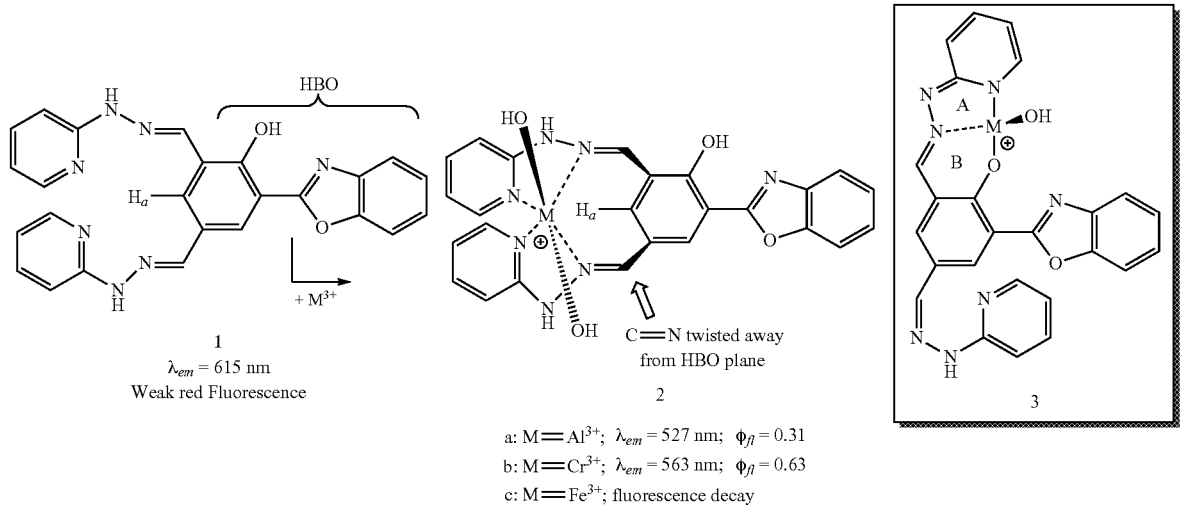

Scheme 4. Dye 1 and its $Cr^{3+}$ complex 2 (3 is possible but not preferred).

a: M=$Al^{3+}$; $\lambda_{em}$ = 527 nm; $\phi_{fl}$ = 0.31
b: M=$Cr^{3+}$; $\lambda_{em}$ = 563 nm; $\phi_{fl}$ = 0.63
c: M=$Fe^{3+}$; fluorescence decay Sensor 1 was synthesized by refluxing the corresponding dialdehyde (as described in W. Chen, Y. Xing, and Y. Pang, *Org. Lett.*, 2011, 13, 1262) with hydrazinopyridine in EtOH proposed binding model, the Mass spectra were carried out. In aqueous medium (10 µM sensor 1 in $H_2O$:EtOH=8:2), the signal of ligand 1 almost disappeared (TOF-MS-ES$^+$ at peak

Figure 13:
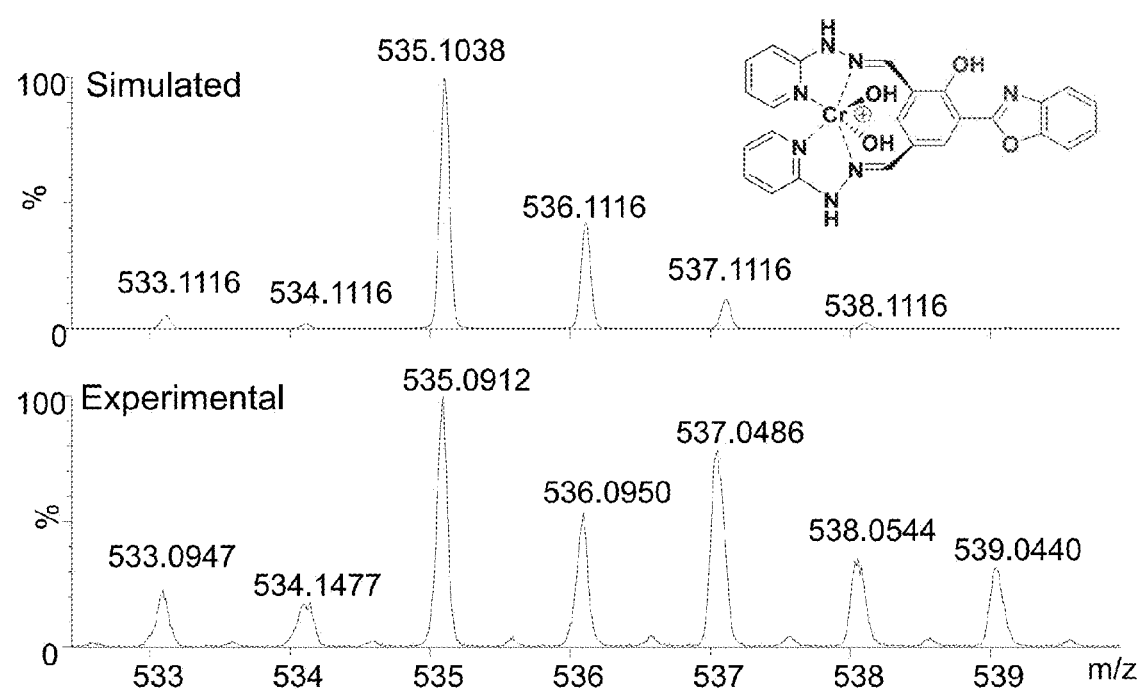
FIG. 13 provides a chart of TOF-Mass-ES$^+$ spectra of dye 1 and its $Cr^{3+}$ complex 2: $[1+ Cr^{3+}+2(OH)^-]^+$.
Figure 14:
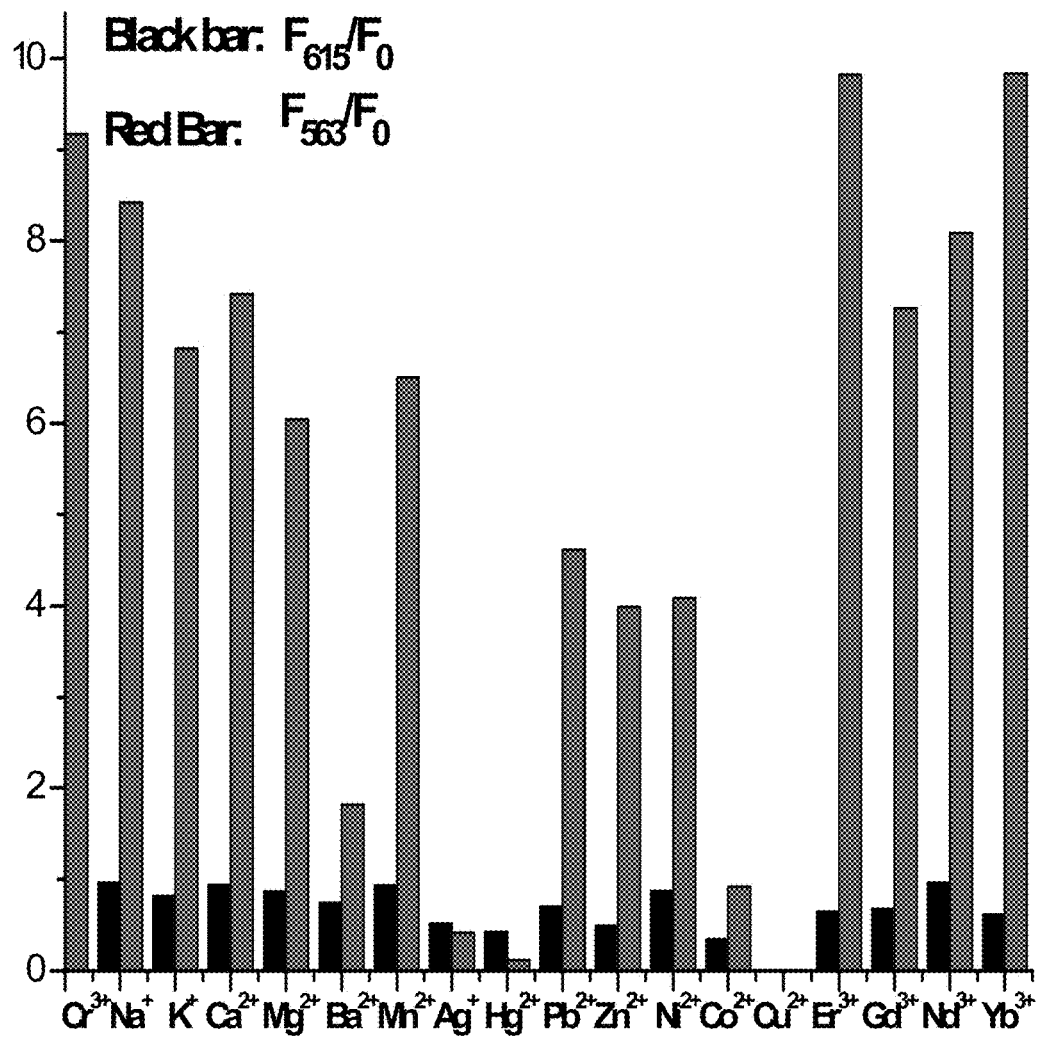
FIG. 14 provides a graph of the emission intensity of 1 (10 μM) at 615 nm in $H_2O$:EtOH=8:2 upon addition of 10.0 equiv of different metal ions excited at 390 nm (Black bars). Red bars represent the fluorescence intensity at 563 nm with subsequent addition of 10 equiv. of $Cr^{3+}$.

[1+Na$^+$]$^+$=472.149) upon addition of Cr$^{3+}$ (or Al$^{3+}$), which tells the clear interaction of ligand 1 to both trivalent metal ions Al$^{3+}$ and Cr$^{3+}$ in water. Furthermore, in Cr$^{3+}$ detection, the newly formed positively charged peak of TOF-MS-ES$^+$ at 535.0912, which matched [1+Cr$^{3+}$+2(OH)$^-$]$^+$=535.1038, indicates the formation of 2 (FIG. 13). The presence of two hydroxy groups was associated with the strong hydration property of Cr$^{3+}$ ion. Similarly, the peak at 510.1091 was also found in the Al$^{3+}$ binding experiment, which matched the isotope pattern for [1+Al$^{3+}$+2(OH)$^-$]$^+$=510.1465.

In order to examine the selectivity of 1, some other cations were added to a solution of 1 under the same conditions. Addition of M$^+$ and M$^{2+}$ cations (10 equiv.) induced almost no change in the UV-vis spectra of 1 (except Cu$^{2+}$). The result indicated the weak binding between dye 1 and the mono- and divalent metal ions. Physiologically important metal ions which exist in living cells, such as Ca$^{2+}$, Mg$^{2+}$, Na$^+$ and K$^+$ gave negligible response. Most heavy and transition metal ions, such as Mn$^{2+}$, Ni$^{2+}$, Pb$^{2+}$, Ba$^{2+}$, Ag$^+$, Hg$^{2+}$ showed slight quenching, and only Cu$^{2+}$ quenched the fluorescence (FIGS. 9 to 12). The emission ratio of $F_{615}/F_0$ was used to plot against various metal ions, where $F_0$ indicates the fluorescence intensity of free 1 while $F_{615}$ indicated the fluorescence intensity upon addition of 10 equiv of the metal ions (FIG. 13, black bars). Addition of one of the metal ions with subsequent addition of Cr$^{3+}$, the green-yellow fluorescence was then turned on (FIG. 13, red bars). Therefore, 1 is a highly selective chemosensor for Cr$^{3+}$.

Figure 15A:
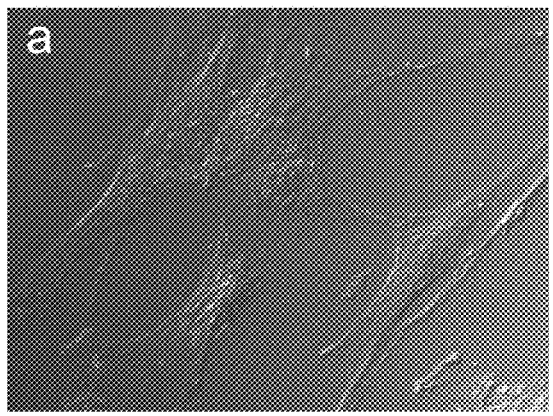
FIG. 15A provides a confocal fluorescence images of Human mesenchymal stem cells (hMSCs) excited with a Diode laser (405 nm) on an Olympus FV-1000 laser scanning microscope. The images were collected at bright field. A→D: The cells were incubated with dye 1 in PBS for 60 mins.
Figure 15D:
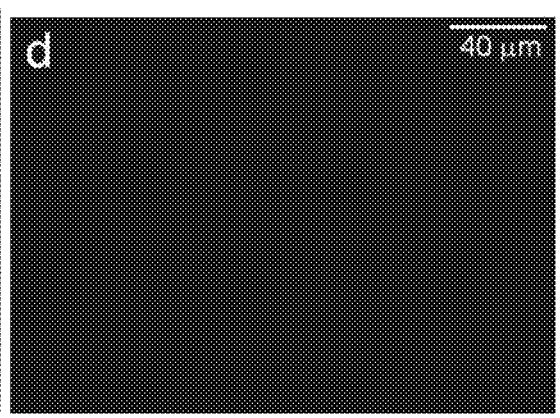
FIG. 15B provides a confocal fluorescence images of Human mesenchymal stem cells (hMSCs) excited with a Diode laser (405 nm) on an Olympus FV-1000 laser scanning microscope. The images were collected at bright field. B→E: The cells were first treated with $Cr^{3+}$ (30 μM) for 30 mins and further exposed to dye 1 (10 μM) in PBS for another 60 mins, and image FIG. 15E was collected from 535-565 nm.
FIG. 15C provides a confocal fluorescence images of Human mesenchymal stem cells (hMSCs) excited with a Diode laser (405 nm) on an Olympus FV-1000 laser scanning microscope. The images were collected at bright field. C→F: The cells were first treated with $Al^{3+}$ (30 μM) for 30 mins and further exposed to dye 1 (10 μM) in PBS for another 60 mins, and image FIG. 15F was collected from 505-525 nm FIG. 15D provides a confocal fluorescence images of Human mesenchymal stem cells (hMSCs) excited with a Diode laser (405 nm) on an Olympus FV-1000 laser scanning microscope. The images were collected fluorescent channels. A→D: The cells were incubated with dye 1 in PBS for 60 mins.
FIG. 15E provides a confocal fluorescence images of Human mesenchymal stem cells (hMSCs) excited with a Diode laser (405 nm) on an Olympus FV-1000 laser scanning microscope. The images were collected fluorescent channels. B→E: The cells were first treated with $Cr^{3+}$ (30 μM) for 30 mins and further exposed to dye 1 (10 μM) in PBS for another 60 mins, and image FIG. 15E was collected from 535-565 nm.
FIG. 15F provides a confocal fluorescence images of Human mesenchymal stem cells (hMSCs) excited with a Diode laser (405 nm) on an Olympus FV-1000 laser scanning microscope. The images were collected fluorescent channels. C→F: The cells were first treated with $Al^{3+}$ (30 μM) for 30 mins and further exposed to dye 1 (10 μM) in PBS for another 60 mins, and image FIG. 15F was collected from 505-525 nm
Figure 15B:
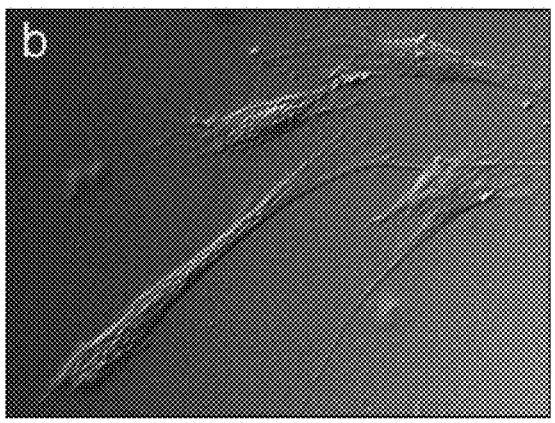
Figure 15E:
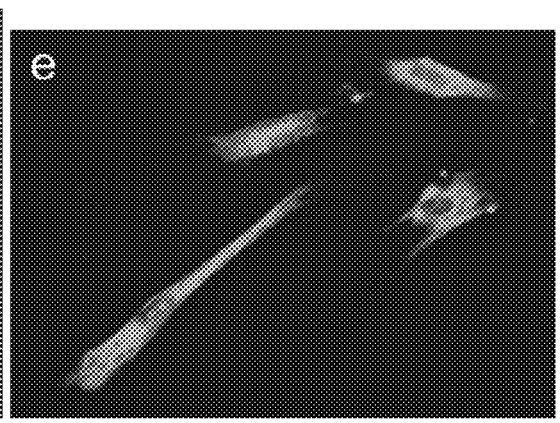
Figure 15C:
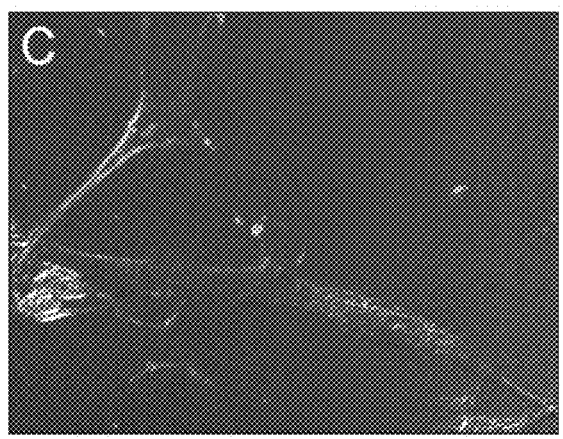
Figure 15F:
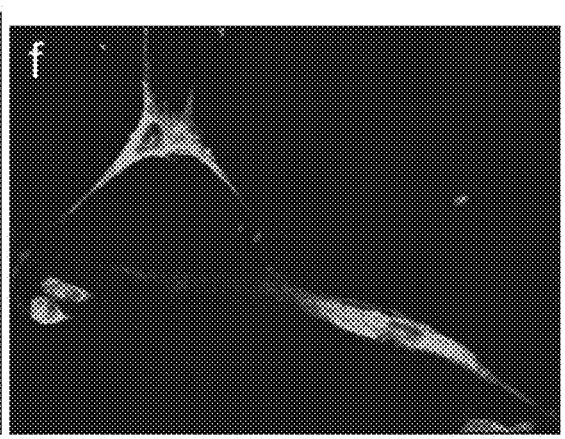

The potential application of 1 for both Cr$^{3+}$ and Al$^{3+}$ in biological samples was examined by using confocal fluorescence microscopy. In the control experiment, staining human mesenchymal stem cells (hMSCs) with 10 μM dye 1 for 30 mins led to negligible intracellular fluorescence (FIG. 15d). When the cells were first incubated with 30 μM of metal ions (Cr$^{3+}$ or Al$^{3+}$) for 30 mins, then further treated with 10 μM sensor 1 for another 30 minutes, a significant increase in the fluorescence from the intracellular area was observed (FIGS. 15e and 15f). Bright-field measurements confirmed that the cells, after being treated with Cr$^{3+}$/Al$^{3+}$ and 1, were viable throughout the imaging experiments. These results demonstrate that the probe is permeable to cells, binds to intracellular Cr$^{3+}$ and Al$^{3+}$, and emits strong fluorescent light, thus is highly suitable for determining intracellular Cr$^{3+}$ and Al$^{3+}$ ions. Response to Cr$^{3+}$ and Al$^{3+}$ ions with distinctly different colors (yellow-green and cyan, respectively) from the cell samples raised the prospect that the Cr$^{3+}$ and Al$^{3+}$ ions could be simultaneously determined and distinguished A single fluorescent molecular probe that can specifically detect trivalent ions (Cr$^{3+}$, Al$^{3+}$ and Fe$^{3+}$) in aqueous medium has been synthesized. In one or more embodiments, the sensor included a trivalent metalcomplexing hydroxyphenylbenzazole compound with two Schiff base moieties to bind trivalent cations Al$^{3+}$, Cr$^{3+}$ and Fe$^{3+}$ (M$^{3+}$ cation), while being silent to nearly all other metal ions. In these or other embodiments, the sensor utilized two "hydrazone Schiff base" to bind trivalent cations Al$^{3+}$, Cr$^{3+}$ and Fe$^{3+}$ (M$^{3+}$ cation), while being silent to nearly all other metal ions. Simultaneous binding to two "hydrazone Schiff base" by M$^{3+}$ cation removed the fluorescence "quenching effect" associated with Schiff base, thereby leading to great fluorescence turn-on. Different from most other sensors, binding of the trivalent metal ions (Al$^{3+}$, Cr$^{3+}$ and Fe$^{3+}$) caused the notable spectral shift, as the ESIPT emission from HBO is sensitive to electronic perturbation. Large response from both fluorescence intensity and spectral (nm) shift provided distinctly different profile for each of three trivalent metal ions, thereby allowing their naked eyed detection. By using the cation binding event to turn-on the ESIPT emission, the study thus illustrates an effective strategy that not only selectively detects Al$^{3+}$, Cr$^{3+}$ and Fe$^{3+}$, but also clearly differentiates them. Cell imaging of confocal fluorescence microscopy further demonstrated that 1 can be used for monitoring intracellular Cr$^{3+}$ and Al$^{3+}$ levels in living cells. Due to the importance of Cr$^{3+}$ and Al$^{3+}$ in biological systems, and the lack of successful examples for the imaging of both Cr$^{3+}$ and Al$^{3+}$, we anticipate that this probe will be of great benefit to biomedical researchers for studying the bioactivity of Cr$^{3+}$ and Al$^{3+}$ in biological systems.

Various modifications and alterations that do not depart from the scope and spirit of this invention will become apparent to those skilled in the art. This invention is not to be duly limited to the illustrative embodiments set forth.

What is claimed is:

1. A hydroxyphenylbenzazole compound containing a Schiff base moiety, the compound comprising:
    a 2-hydroxyphenyl group bound to a single benzazole group;
    a first ligand group that is a first Schiff base moiety; and a second ligand group selected from the group consisting of a second Schiff base moiety and a hydroxyl group, where the first Schiff base moiety and the second Schiff base moiety may be the same or different, and at least one of the first Schiff base moiety and the second Schiff base moiety is defined by the formula

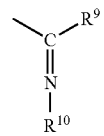

where R$^9$ is a hydrogen atom or a monovalent organic group, and R$^{10}$ is a monovalent organic group that includes an atom with a lone pair of electrons.

2. The hydroxyphenylbenzazole compound containing a Schiff base moiety of claim 1, where the benzazole group is a benzoxazole group.

3. The hydroxyphenylbenzazole compound containing a Schiff base moiety of claim 1, where the benzazole group is a benzothiazole group.

4. The hydroxyphenylbenzazole compound containing a Schiff base moiety of claim 1 where the benzazole group is a benzimidazole group.

5. The hydroxyphenylbenzazole compound containing a Schiff base moiety of claim 1, where at least one of the first Schiff base moiety and the second Schiff base moiety is a Schiff base selected from the group consisting of:

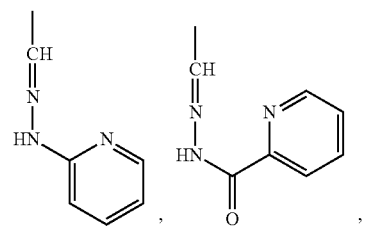

-continued

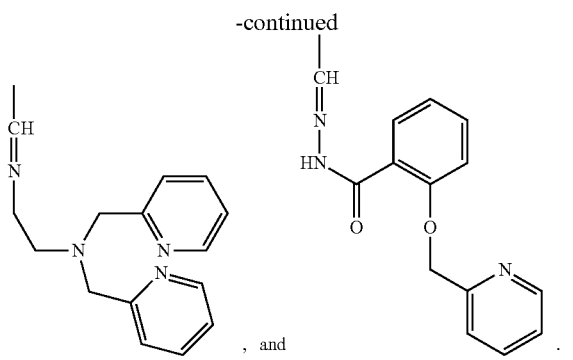
, and

6. The hydroxyphenylbenzazole compound containing a Schiff base moiety of claim 1, where the hydroxyphenylbenzazole compound containing a Schiff base moiety is defined by the formula

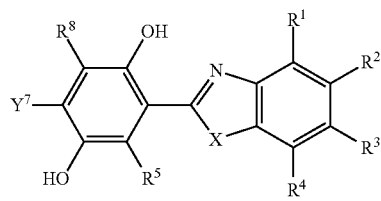

where X is an oxygen atom, a sulfur atom, a nitrogen atom with a pendant hydrogen atom, or a nitrogen atom with a pendant alkyl group; $Y^7$ is the first Schiff base moiety, and $R^1$, $R^2$, $R^3$, $R^4$, $R^5$, and $R^8$ are each individually a hydrogen atom or a monovalent organic group.

7. The hydroxyphenylbenzazole compound containing a Schiff base moiety of claim 1, where the hydroxyphenylbenzazole compound containing a Schiff base moiety is defined by the formula

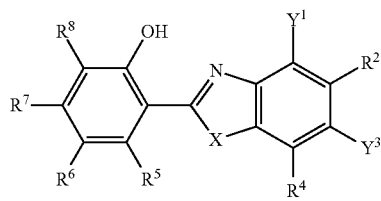

where X is an oxygen atom, a sulfur atom, a nitrogen atom with a pendant hydrogen atom, or a nitrogen atom with a pendant alkyl group; $Y^1$ and $Y^3$ are each individually a Schiff base moiety, and $R^2$, $R^4$, $R^5$, $R^6$, $R^7$, and $R^8$ are each individually a hydrogen atom or a monovalent organic group.

8. The hydroxyphenylbenzazole compound containing a Schiff base moiety of claim 1, where the hydroxyphenylbenzazole compound containing a Schiff base moiety is defined by the formula

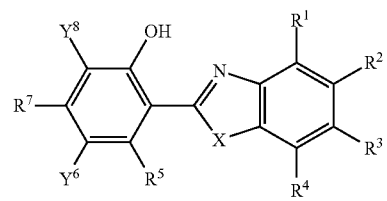

where X is an oxygen atom, a sulfur atom, a nitrogen atom with a pendant hydrogen atom, or a nitrogen atom with a pendant alkyl group; $Y^6$ and $Y^8$ are each individually a Schiff base moiety, and $R^1$, $R^2$, $R^3$, $R^4$, $R^5$, and $R^7$ are each individually a hydrogen atom or a monovalent organic group.

9. A hydroxyphenylbenzazole compound containing a Schiff base defined by the formula

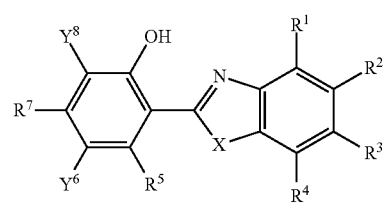

where X is an oxygen atom, a sulfur atom, a nitrogen atom with a pendant hydrogen atom, or a nitrogen atom with a pendant alkyl group; $Y^6$, $Y^7$, and $Y^8$ are each individually a hydrogen atom, a Schiff base moiety, or a hydroxyl group, $R^1$, $R^2$, $R^3$, $R^4$, and $R^5$ are each individually a hydrogen atom or a monovalent organic group; with the proviso that at least one of $Y^6$, $Y^7$, and $Y^8$ is a Schiff base moiety defined by the formula

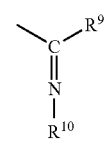

where $R^9$ is a hydrogen atom or a monovalent organic group, and $R^{10}$ is a monovalent organic group that includes an atom with a lone pair of electrons.

10. A method for detecting the presence of metal ions, comprising the steps of:
(a) contacting a test sample with a hydroxyphenylbenzazole compound containing a Schiff base moiety, the compound comprising:
a 2-hydroxyphenyl group bound to a single benzazole group;
a first ligand group that is a first Schiff base moiety; and
a second ligand group selected from the group consisting of a second Schiff base moiety and a hydroxyl group, where the first Schiff base moiety and the second Schiff base moiety may be the same or different, and at least one of the first Schiff base moiety and the second Schiff base moiety is defined by the formula

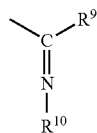

where $R^9$ is a hydrogen atom or a monovalent organic group, and $R^{10}$ is a monovalent organic group that includes an atom with a lone pair of electrons (b) exciting the hydroxyphenylbenzazole compound containing a Schiff base moiety with an excitation wavelength to induce a fluorescence response; and (c) observing a fluorescence response emission.

11. The method of claim 10, where the hydroxyphenylbenzazole compound containing a Schiff base moiety is defined by the formula

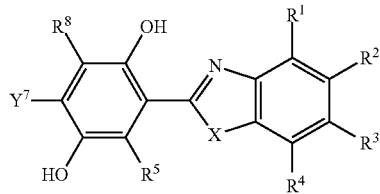

where X is an oxygen atom, a sulfur atom, a nitrogen atom with a pendant hydrogen atom, or a nitrogen atom with a pendant alkyl group; $Y^7$ is the first Schiff base moiety, and $R^1$, $R^2$, $R^3$, $R^4$, $R^5$, and $R^8$ are each individually a hydrogen atom or a monovalent organic group.

12. The method of claim 11, where the hydroxyphenylbenzazole compound containing a Schiff base moiety is used to detect a zinc ion, and the observation of a near-infrared response indicates the detection of zinc.

13. The method of claim 10, where the hydroxyphenylbenzazole compound containing a Schiff base moiety is defined by the formula

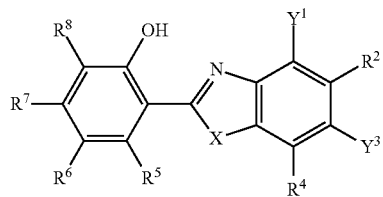

where X is an oxygen atom, a sulfur atom, a nitrogen atom with a pendant hydrogen atom, or a nitrogen atom with a pendant alkyl group; $Y^1$ and $Y^3$ are each individually a Schiff base moiety, and $R^2$, $R^4$, $R^5$, $R^6$, $R^7$, and $R^8$ are each individually a hydrogen atom or a monovalent organic group.

14. The method of claim 13, where the hydroxyphenylbenzazole compound containing a Schiff base moiety is used to detect the presence of a metal cation selected from $Fe^{3+}$, $Cr^{3+}$, and $Al^{3+}$.

15. The method of claim 10, where the hydroxyphenylbenzazole compound containing a Schiff base moiety is defined by the formula

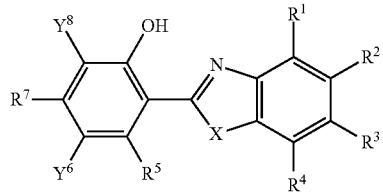

where X is an oxygen atom, a sulfur atom, a nitrogen atom with a pendant hydrogen atom, or a nitrogen atom with a pendant alkyl group; $Y^6$ and $Y^8$ are each individually a Schiff base moiety, and $R^1$, $R^2$, $R^3$, $R^4$, $R^5$, and $R^7$ are each individually a hydrogen atom or a monovalent organic group.

16. The method of claim 15, where the hydroxyphenylbenzazole compound containing a Schiff base moiety is used to detect the presence of a metal cation selected from $Fe^{3+}$, $Cr^{3+}$, and $Al^{3+}$.

17. The method of claim 10, where the test sample includes living cells or a living organism.

* * * * *